US007335640B2

(12) United States Patent
Siegel et al.

(10) Patent No.: US 7,335,640 B2
(45) Date of Patent: *Feb. 26, 2008

(54) ADMINISTRATION OF HYPOCRETIN-1 FOR TREATMENT OF NARCOLEPSY

(75) Inventors: Jerome M. Siegel, Northridge, CA (US); Joshi John, Northridge, CA (US); Ming-Fung Wu, Northridge, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/461,044

(22) Filed: Jul. 31, 2006

(65) Prior Publication Data

US 2007/0010445 A1    Jan. 11, 2007

Related U.S. Application Data

(63) Continuation of application No. 09/569,835, filed on May 11, 2000, now Pat. No. 7,112,566, which is a continuation-in-part of application No. 09/398,260, filed on Sep. 17, 1999, now Pat. No. 6,204,245.

(60) Provisional application No. 60/194,572, filed on Apr. 4, 2000.

(51) Int. Cl.
| | |
|---|---|
| *A61K 38/17* | (2006.01) |
| *A61K 39/00* | (2006.01) |
| *A61K 39/38* | (2006.01) |
| *A61K 39/385* | (2006.01) |
| *A01N 37/18* | (2006.01) |

(52) U.S. Cl. .......................... 514/12; 514/2; 424/198.1; 424/184.1; 424/185.1; 424/193.1; 424/924; 530/350; 435/7.1

(58) Field of Classification Search ...................... None
See application file for complete search history.

(56) References Cited

U.S. PATENT DOCUMENTS

| | | | |
|---|---|---|---|
| 3,980,665 | A | 9/1976 | Fahnenstich et al. |
| 5,196,308 | A | 3/1993 | Nepon et al. |
| 5,541,065 | A | 7/1996 | Erlich et al. |
| 5,565,548 | A | 10/1996 | Neurath et al. |
| 5,908,749 | A | 6/1999 | Mignot et al. |
| 5,912,250 | A | 6/1999 | Shintzky et al. |
| 2005/0048538 | A1 | 3/2005 | Mignot et al. |

FOREIGN PATENT DOCUMENTS

WO    WO 01-08720 A3    2/2001

OTHER PUBLICATIONS

Aldrich, M., "Narcolepsy and Related Disorders," Sleep Medicine, Chapter 10, pp. 152-174; Oxford University Press, New York, NY USA (1999).
Aldrich, M., S., "Narcolepsy ," New Eng. J. Med., 323389-394 (1990).
Alrich, M. S., "Narcolepsy," Neurology, 42(Suppl. 6): 34-43 (1992).
Aldrich, M.S., "The Neurobiology of Narcolepsy," TINS, 14(6):235-239 (1991).
Aldrich, M.S., "Diagnostic aspects of narcolepsy," Neurology, 50(suppl. 1):S2-S7 (1991).
Baker et al., "Canine narcolepsy-cataplexy syndrome: evidence for an inherited monoaminergic-cholinergic imbalance," Brain Mechnisms of Sleep, edited by McGinty et al.; New York: Raven Press, pp. 199-233 (1985).
Behar et al., "A New DRBI 12022 LLELE (drbi 12022) found in associatio with DQA1 0102 and DQB1 0602 in two black narcoleptic subjects," Immunogenetics, 41:52 (1995).
Billiard, M., "Narcolepsy, Clinical Features and Aetiology," Ann. Clin. Res., 17:220-226 (1985).
Billiard et al., "Elevated antibodies to streptococcal antigens in narcoleptic subjects," Sleep Res., 18:201, (1989), abstract only.
Broughton et al., "Psychosocial impact of narcolepsy," Sleep, 17:S45-S49 (1994).
Cadieux, R., et al., "Pharmacologic and psychotherapeutic issues in coexistent paranoid schizophrenia and narcolepsy: case report" J. Clin. Psychol. 1985, 46: 191-193.
Cederberg et al., "Breeding history of the Stanford colony of narcoleptic dogs," Vet. Rec., 142 31-36 (1998).
Chemelli, R. M. et al., "Narcolepsey in orexin knockout mice: molecular genetics of sleep regulation," Cell 98: 437-451 (1999).
Chen, et al., "intracisternal administration of orexins increased blood pressure and heart rate urethane anesthetized rats," Spc Neurosci Abst 25:12 (1999).
Delashwaw et al., "Cholinergic Mechanisms and Cataplexy in Dogs," Exp Neurology, 66:745-757 (1979).
Douglass et al., Three Simultaneous Major Sleep Disorders,: Can. J. Psyciatry, 32(1): 57-60 (1987).
Douglass, A., et al., "Florid refractory schizophrenias that turn ouit to be treatable variants of HLA-associated narcolepsy" J. Nerv. Ment Dis. (1991) 179: 12-17.
Douglass et al., "Monozygotic twins concordant for the narcoleptic syndrome," Neurology, 39(1): 140-141 (1989).
DSM-IV, fourth edition, 1994 APA, pp. 551-552.
Dube M. G., et al., "Food intake elicited by central administration of orexin/hypocretins: identification of hypothalamic sites of action," Brain Res. 842: 473=477 (1999).

(Continued)

*Primary Examiner*—Olga N. Chernyshev
(74) *Attorney, Agent, or Firm*—Townsend and Townsend and Crew LLP

(57)    ABSTRACT

The invention provides compositions and methods for treatment of sleep disorders. Such methods entail administering to the patient a therapeutically effective dosage regime of an agonist of a hypocretin 1 (Hcrt-1) receptor to a peripheral tissue of the patient, and monitoring the condition of the patient responsive to the treatment, wherein the monitoring indicates a reduction in excessive daytime sleepiness (EDS) and an improvement in nighttime sleep consolidation and architecture. The methods are particularly useful for prophylactic and therapeutic treatment of one or more sleep disorders in a patient.

18 Claims, 4 Drawing Sheets

OTHER PUBLICATIONS

Erlich et al., "Narcolepsy: A Neuropathologic Study," Sleep, 9:126-132 (1986).
Foutz et al., "Genetic Factors in Canine Factors in Canine Narcolepsy," Sleep, 1(4):413-421 (1979).
Fredrickson et al., "CSF immune variables in patients with narcolepsy," Acta. Neurol. Scan., 81:253-254 (1990).
Fry, J.M., "Treatment modalities for narcolepsy," Neurology, 50(Suppl 1): S43-S48 (1998).
Fujiki, Nobuhiro et al., "Effects of IV and ICV Hypocretin-1 (Orexin A) In Hypocretin Receptor-2 Gene Mutated Narcoleptic Dogs And IV Hypocreton-1 Replacement Therapy In A Hyprcretin-Ligand-Deficient Narcoleptic Dog," Sleep, vol. 26, No. 8, pp. 953-959 (2003).
Gaiser et al., "Evidence for an autoimmune etiplogy in canine narcolepsy," Sleep Res., 18:230 (1989) abstract only.
Gibson et al., HLA and Schizophreina: Refutation of Reported Associations with A9 (A23/A24), DR4, and DQβ1 0602,∀ Aμ. θ.Μεδ. Γενεηχσ, 88:416-421 (1999).
Green et al., "Narcolepsy Signs, Symptoms, Differential Diagnosis, and Management," Arch. Fa. Med., 7:472-478 (1998).
GroBkppf et al., "Potential role for the narcolepsy-anmd multiple sclerosis-associated HLA allele DQB1 0602 in schizophrenia subtypws," Schizophrenia Research, 30:187-189 (1998).
Guilleminault et al., "Investigations into the neurologic basis of narcolepsy," Neurology, 50(Suppl. 1):S8-S15 edited by Fry, J.M. (1998).
Guilleminault, C., "Narcolepsy Syndrome", Principles and Practice of Sleep Medicine, 2nd edition, pp. 549-561, 1993.
Guilleminault et al., "Prazosin Contraindicated in Patients with Narcolepsy," The Lancet, 2(8609):511 (1988).
Hagan, J. J. et al., "Orexin A activates locus coruleus cell firing and increases arousal in the rat," Proc Natl Acad Sci U.S.A. 96:10911-10916 (1999).
Hanson, Leah R. et al., "Intranasal Administration of Hypocretin 1 (Orexin A) Bypasses The Blood-Brain Barrier & Targets The Brain: A New Strategy For The Treatment OF Narcolepsy," Drug Delivery Technology, vol. 4, No. 4, 10 pages May 2004.
Hinze-Selch et al., "In vivo and in vitro immune variables in Patients with narcolepsy and HLA-DR2 matched controls," Neurology, 50:1149-1152 (1998).
Honda et al., "Genetic Aspects of Narcolepsy," in Handbook of Sleep Disorders, edited by M. Thorpy; (Marcel Dekket, Inc., New York, NY) (1990), pp. 217-234.
Honda et al., "HLA-DR2 and Dw2 in narcolepsy and in other disorders of excessive somnolence without cataplexy," Sleep, 9(1):133-142 (1986).
Hublin et al., "The preva;ence of narcolepsy: and epidemiological study of the Finnish twin cohort," Ann. Neurol., 35(6):709-716 (1994).
Jacob et al., "Heritable major hostocompatibility complex Class II-associated differences in production of tumor necrosis factor and relevance to genetic predisposition to systemic lupus erythematosus," PNAS, 87:1233-1237 (1990).
John, et al., Hypocretin-1 reduces cataplexy and normalizes sleep and walking durations in narcoleptic dogs sleep, vol. 23, DRAFT Abstract, available on meeting webpage for all meeting authors to review, Mar. 6-9, 2000.
John, et al., Hypocretin-1 reduces cataplexy and normalizes sleep and waking durations in narcoleptic dogs sleep, vol. 23, Abstract Supplement 2, A 11-12, Apr. 15, 2000.
Kaitin et al., "Evidence for excessive sleeponess in canine narcoleptics," Electroencheph. Clin. Neurophysiol., 64:447-454 (1986).
Kanbayashi et al., "Thalidomide, a hypnotic with immune modulating propertied, increases cataplexy in canine narcolepsy," Neuroreport, 7(12):1881-1886 (1996).
Kastin, A. J. and Akerstrom, V. (1999) "Orexin A but not orexein B rapidly enters brain from blood by simple diffusion," J Pharmacol Exp Ther 289: 219-223.

Kilduff et al., "Immunosuppression with Cyclosporine as a Treatment for Canine Narcolepsy," Sleep Research, 16:369 (1987) abstract.
Klippel et al., Rhematology, second edition, cover page and table of contents, London:Mosby (1998).
Krueger et al., "Cytokines in sleep regulation," Slee and sleep disorders: from molecule to behavior, edited by Hayaishi and Inoue; pp. 261-277; Tokyo; Academic Press (1997).
Langdon et al., "Immune factors in Narcolepsy," Sleep, 9(1):143-148 (1986).
Lin et al. Cell, 1999, 98, 99 365-376.
Lin, L. et al., "The REM sleep disorder canine narcolepsy is caused by a mutation in the hypocretin (orexin) recepton gene" Cell 98: 365-376. (1999).
Matsuki et al., "No male segregation distortion of DR2 Haplotypes in Japanese narcoleptic patients," Human Immunology, 23:23-26 (1988).
Matsuki et al., "HLA in Narcolepsy in Japan," chapter 3 from HLA in Narcolepsy, edited by Honda and Juji, pp. 58-76; New York: Springer Verlag (1988).
Matsuki et al., "DQ (rather than DR) genme marks susceptibility to narcolepsy," Lancet, 339:1052 (1992).
Mignot et al., "Genetic linkage of autosomal recessive canine narcolepsy with a μ immunoglobulin heavy-chain switch-like segment," PNAS, 88:3475-3478 (1991).
Mignot E. et al., "DQB1 0602 and DQA1 0102 (DQ1) Are better Markers Than Dr1 for Narcolepsy in Caucasian and Black Americans," Sleep, 17:S60-S67 (1994).
Mignot, E., "Genetic and familial aspects of narcolepsy," Neurology, 50(2)(Suppl 1):S16-S22 (1998).
Mignot et al., "Effect of α1-adrenoceptors blockade with prazosin in canine narcolepsy," Brain Res., 444:184-1888 (1988).
Mignot, E. et al., "Narcolepsy and immunity," Adv. Neuroimmunol., 5:23-37 (1995).
Mignot, E. et al., "Canine cataplexy is preferentiallty controlled by adrenergic mechanisms: evidence using monoamine selective uptake inhibitors and release enhancers," Psychopharmacology, 113:76-82 (1993).
Mignot, E. et al., "Nocturnal Sleep and Daytime Sleepiness in normal Subjects with HLA-DQB1 0602," Sleep, 22(3):347-352 (1999).
Mitler, M. M. "Toward an animal model of narcolepsy-cataplexy," chapter 24 from Narcolepsy, edited by Guilleminault, Dement and Passouant; pp. 387-409; New York:Spectrum Publications, Inc. (1975).
Mitler et al., "Narcolepsy Diagnosis, Treatment, and Management," Psych. Clin. N. Amer., 10(4):593-606 (1987).
Mitler, M. M. et al., "treatment of Narcolepsy with Methamphetamine," Sleep, 16(4):306-317 (1993).
Mitler, M. M., "Evaluation of Treatment With Stimulants in Narcolepsy," Sleep, 17:S103-S106 (1994).
Montplaisir et al., "Streptococcal antibodies in narcolepsy and idiopathic hypersoimnia," Sleep Res., 18:271 (1989).
Motoyama et al., "Restriction fragment length polymorphism in canine narcolepsy," Immunogenetics, 29:124-126 (1989).
Mueller-Ecjhardt et al., "Is there an infectious origin of narcolepsy?," The Lancet, 424 (1990).
Nishino, S. et al., "Desmethyl Metabolites of Serotonergic Uptake Inhibitors Are More Potent for Supressing Cannine Cataplexy Than their Parent Compounds," Sleep, 16:706-712 (1993).
Nishino, S. et al., "Hypocretin (orexin) deficiency in human narcolepsy" The Lancet 355: 39-40 (2000).
Nishino, S. et al., "Pharmacological aspects of human and canine narcolepsy," Prog. Neurobiol., 52:27-78 (1997).
Opp et al., "Interleukin-10 (cytokine synthesis inhibitory factor) acts in the central nervous system of rats to reduce sleep," J. Neuroimmunol., 60:165-168 (1995).
Peyron et al., "A mutation in case of early onset narcolepsy and a generalized absence of hypocretin peptides in human narcoleptic brains," Nature Medicine 6:991-997 (2000).
Pollmacher et al., "DR-2 Positive monizygotic twins discordant for narcoepsy," Sleep, 13(4):336-343 (1990).

Robinson et al., "Narcolepsy," chapter 25 from Sleep Disorders Medicine: Basic Science, Technical Considerations, and Clinical Aspects, edited by Chokroverty, S.; Butterworth Heinemann Boston, MA USA (1999) pp. 427-220.

Rubin et al., "HLA-DR2 association with excessive somnolence in narcolepsy does not generalize to sleep apnea and is not accomplanied by systemic autoimmune abnormalities," Clin. Immunol. Immunbopathol., 49:149-158 (1988).

Siegel, J.M. et al., "Neuronal degeneration in canine narcolepsy," J. Neuroscience, 19(1)248-257 (1999).

Sinha et al., "Autoimmune Diseases: The Failure of Self Tolerance," Science, 248:1380-1388 (1990).

Stein et al., "Glucocorticoids," chapter 50 from Texbook of Rheymathology, edited by Kelly et al.; pp. 787-803 (1997).

Tafti et al., "Major histocompatibility Class II molecules in the CNS: increased microglial expression at the onset of narcolepsy in canine model.," J, Neurosci., 16(15):4588-4595 (1996).

Takahashi, N. et al., "Stimulation of gastric acid secretion by centrally administered orexin- A in conscious rats" Biochem Bipphys Res Commun 254: 623-627 (1999).

Vgnotzas, A. N. et al., "Sleep and It's Disorders," Annu. Rev. Med., 50:387-400 (1999).

Xi et al., "microinjection of orxin-A (hypocretin-1) into the laterodorsal tegmental nucleus of the cat: effects on sleep and waking states," Society for Neuroscience Abstracts 26:15 (2000).

Yoss et al., "Narcolepsy in children," Pediatrics, 25:1025-1033 (1960).

Mignot et al., "*Nocturnal Sleep and Daytime Sleepiness in Normal Subjects with HLA-DQB1*0602*," SLEEP, vol. 22, No. 3, 1999, Center for Narcolepsy, Stanford University, Department of Psychiatry and Behavioral Sciences, pp. 347-352.

Different days of cataplexy test

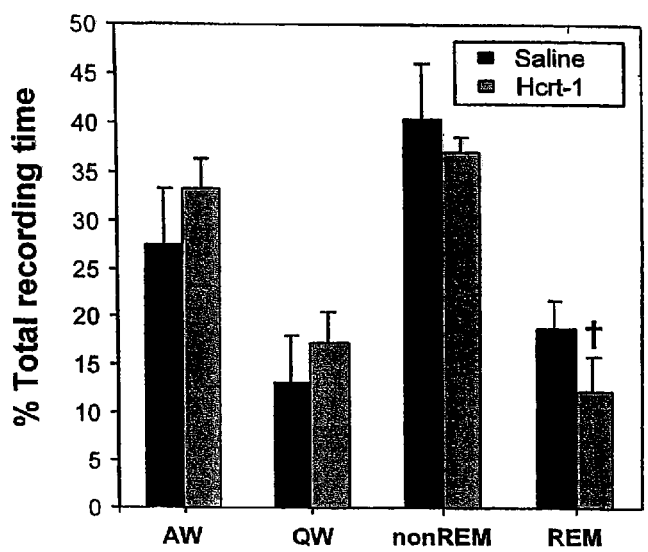
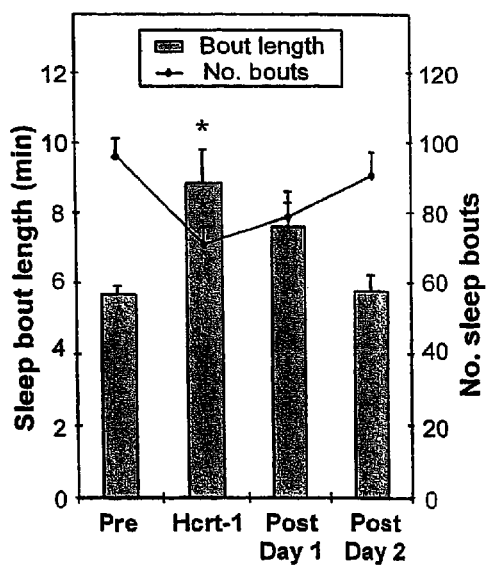
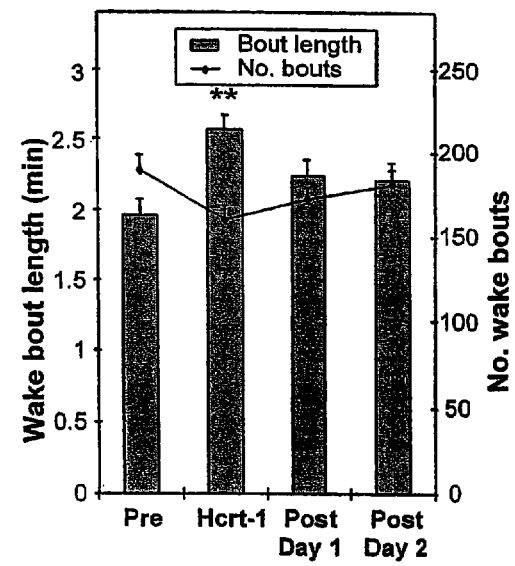

ADMINISTRATION OF HYPOCRETIN-1 FOR TREATMENT OF NARCOLEPSY

CROSS-REFERENCES TO RELATED APPLICATIONS

This application is a continuation of U.S. patent application Ser. No. 09/569,835, entitled "SYSTEMIC ADMINISTRATION OF HYPOCRETIN-1", filed on May 11, 2000 now U.S. Pat. No. 7,112,566; which is a continuation-in-part of U.S. Pat. Appl. No. 09/398,260 filed Sep. 17, 1999 Issued U.S. Pat. No. 6,204,245, entitled "TREATMENT OF NARCOLEPSY WITH IMMUNOSUPPRESSANTS", and claims the benefit of U.S. Provisional Application No. 60/194,572, entitled "SYSTEMIC ADMINISTRATION OF HYPOCRETIN-1 REDUCES CATAPLEXY AND NORMALIZES SLEEP AND WAKING DURATIONS IN NARCOLEPTIC DOGS, filed Apr. 4, 2000, of which applications are hereby incorporated by reference for all purposes, and the specific purposes described therein and herein.

STATEMENT AS TO RIGHTS TO INVENTIONS MADE UNDER FEDERALLY SPONSORED RESEARCH AND DEVELOPMENT

This invention was made with Government support under Grant No. NS14610, awarded by the National Institutes of Health; and the Veterans Administration. The Government has certain rights in this invention.

TECHNICAL FIELD

This invention resides in the fields of neurology, immunology, and medicine and relates to the treatment of sleep disorders and compositions useful therein.

BACKGROUND OF THE INVENTION

Narcoleptic patients experience cataplexy, which is a sudden loss of muscle tone most commonly in response to the sudden onset of strong emotions, excessive daytime sleepiness and fragmentation of sleep during the night. Current drug treatments can be dichotomized into those that are aimed at daytime sleepiness, typically using dopamine agonists or psychostimulants, and those that are aimed at cataplexy, typically using tricyclic antidepressants. Drug side effects, residual sleepiness and cataplexy episodes continue to be major problems for most treated narcoleptics (Aldrich, M. S., 1998, Neurology 50: S2-S7).

It has been reported that narcolepsy is linked to dysfunction of the newly discovered hypocretin (Hcrt) (orexin) peptide system. This report was based on a deletion in the transcripts of the hypocretin receptor 2 (Hcrt-2) gene in narcoleptic Dobermans and Labradors (Lin, L. et. al., *Cell* (1999) 97: 365-376). A mutation in the gene responsible for the hypocretin-2 (Orexin-2) receptor was reported to be a genetic cause of canine narcolepsy (Lin, L. et al., 1999, *Cell* 98: 365-376). A null mutation of the gene encoding the two known hypocretin (Hcrt) peptides produces aspects of the narcolepsy syndrome in mice (Chemelli, R. M. et al., 1999, *Cell* 98: 437-451). Human narcoleptics have reduced levels of Hcrt-1 in their cerebrospinal fluid (Nishino, S. et al., 2000, *The Lancet* 355: 39-40).

Basic research on the behavioral effects of the hypocretins has generally used intracerebroventricular or intra-parenchymal microinjection of the peptide (Hagan, J. J. et al., 1999, *Proc Natl Acad Sci U.S.A.* 96: 10911-10916; Dube M. G., et al, *Brain Res.* 842: 473-477). The results in this area are controversial. Some studies have concluded that Hcrts administered systemically do not cross the blood-brain barrier (BBB) at sufficient levels to affect physiological function (Chen, C-T et al., 1999, *Soc Neurosci Abst* 25: 12; Takahashi, N. et al, 1999, *Biochem Biophys Res Commun* 254: 623-627), making development of an Hcrt receptor agonist with good BBB permeability a high priority. One group reported that iodinated Hcrt-1 passes the BBB (Kastin, A. J. and Akerstrom, V., 1999, *J Pharmacol Exp Ther* 289: 219-223.) but iodination is known to increase BBB permeability. This result does not remove the question whether the native peptide will pass the BBB.

SUMMARY OF THE INVENTION

In one aspect, the invention provides methods of treating a sleep disorder in a patient. Some methods entail administering to the patient a therapeutically effective dosage regime of an agonist of a hypocretin receptor. In some such methods, the agonist is hypocretin-1 or hypocretin-2. In some such methods, the agonist is a natural human hypocretin-1 or hypocretin-2. In some such methods, the therapeutically-effective dosage regime is administered to a peripheral tissue of the patient, whereby the agonists crosses the blood brain barrier of the patient. In some such methods, the patient experiences a reduction in excessive daytime sleepiness responsive to the administering. In some such methods, the patient experiences an improvement in nighttime sleep consolidate and architecture responsive to the treatment. In some methods, monitoring the condition of the patient responsive to administering the therapeutically effective dosage regime is performed. In some such methods, the monitoring indicates a reduction in excessive daytime sleepiness and an improvement in nighttime sleep consolidation and architecture.

In another aspect, the invention provides methods of treating a sleep disorder in a patient that entail administering to the patient a therapeutically effective dosage regime of hypocretin 1 (Hcrt-1) to a peripheral tissue of the patient, and monitoring the condition of the patient responsive to the treatment. In some such methods, the monitoring indicates a reduction in excessive daytime sleepiness (EDS) and an improvement in nighttime sleep consolidation and architecture. In some such methods, the patient is human.

In some methods, the sleep disorder is narcolepsy, cataplexy, REM sleep behavior disorder, sleep apnea, and insomnia. In some such methods, the hypocretin 1 is free of a label. In some such methods, the therapeutically effective dosage regime is administered after diagnosis of one or more sleep disorders. In some such methods, the hypocretin 1 (Hcrt-1) is administered together with a pharmaceutically acceptable carrier as a pharmaceutical composition.

For treatment of patients susceptible to or suffering from one or more sleep disorders, the dosage in the regime is separated by at least 12 hours. In some treatment regimes, the dosage in the regime is separated by at least 24 hours. In some such treatment regimes, the dosage is 0.3 to about 10 μg/kg of hypocretin 1 (Hcrt-1).

The Hcrt-1 is typically administered by intravenous infusion, transdermal delivery, intramuscular delivery, subcutaneous delivery, oral delivery, or by inhalation. In some such methods, Hcrt-1 is administered by intravenous infusion. In other such methods, Hcrt-1 is administered by oral delivery. Typically, the patient is monitored following administration to assess the effects of treatment. Some such monitoring includes conducting a nocturnal polysomnogram (PSG), Multiple Sleep Latency Test (MSLT), Epworth Sleepiness Scale (EPS) questionnaire, Maintenance of Wakefulness Test (MWT), pupilography, electroencephalograms, electroencephalographic spectral analysis, actigraphy, or maintaining a log of incidence of cataplexy including their number, severity and duration. Other methods of monitoring include conducting immune or histological assays to determine the presence or absence of neurodegeneration, nerve cell death, T cell infiltration, B cell infiltration, monocytic infiltration, apoptosis, or necrosis.

In another aspect, the invention provides methods of diagnosing a sleep disorder in a patient. Such methods entail assaying for the presence of detectable levels of Hcrt-1 or hypocretin 2 (Hcrt-2) in the cerebrospinal fluid or blood serum of a patient.

In another aspect, the invention provides pharmaceutical compositions for treating a sleep disorder in a patient, comprising a therapeutically effective dosage of Hcrt-1 and a pharmaceutically acceptable carrier to reduce daytime sleepiness and improve nighttime sleep consolidation and architecture.

The invention further provides methods of treating schizophrenia in a patient. Such methods entail administering to the patient a therapeutically effective dosage regime of Hcrt-1 to a peripheral tissue of the patient, and monitoring the condition of the patient responsive to the treatment, wherein the monitoring indicates a reduction in excessive daytime sleepiness (EDS) and an improvement in nighttime sleep consolidation and architecture.

The invention further provides methods of treating Alzheimer's in a patient. Such methods entail administering to the patient a therapeutically effective dosage regime of Hcrt-1 to a peripheral tissue of the patient, and monitoring the condition of the patient responsive to the treatment, wherein the monitoring indicates a reduction in excessive daytime sleepiness (EDS) and an improvement in nighttime sleep consolidation and architecture.

The invention further provides methods of treating depression in a patient. Such methods entail administering to the patient a therapeutically effective dosage regime of Hcrt-1 to a peripheral tissue of the patient, and monitoring the condition of the patient responsive to the treatment, wherein the monitoring indicates a reduction in excessive daytime sleepiness (EDS) and an improvement in nighttime sleep consolidation and architecture.

BRIEF DESCRIPTION OF THE DRAWINGS

FIG. 1. Treatment with Hcrt-1 produced short and longer term changes in cataplexy. (FIG. 1C) Three doses of Hcrt-1 produced a complete suppression of cataplexy for three consecutive days. (FIG. 1D) In a more severely affected dog, the administration of five doses of Hcrt-1 produced a complete suppression of cataplexy during the FECT observed on 3 tests given every other day over a 6 day period. (FIG. 1C') and (FIG. 1D'), show the FECT time on the days of the tests in (FIG. 1C) and (FIG. 1D) respectively. Arrows indicate days in which the FECT was done with Hcrt-1 treatment, and doses are indicated in parenthesis. On all the other days animals were tested after the administration of the same volume of saline. (All values in (FIG. 1A) and (FIG. 1B) are mean±SE; P: average of pretreatment days, +p<0.05, ++p<0.01, +++p<0.001 compared to saline control, t-test; *p<0.05, **p<0.01, between doses, Newman-Keuls test. ‡ Indicates no cataplexy attacks observed during the FECT).

FIG. 2. Changes in sleep-wake stages after Hcrt-1 administration. (FIG. 1A) Polygraphic sleep-wake data for the 4 hr periods after Hcrt-1 (3 µg/kg) in comparison to the same periods after normal saline shows a significant decrease in REM sleep. (FIG. 1B) Sleep-wake actigraph data shows a significant increase in sleep bout duration and a decrease in frequency during the dark period after Hcrt-1. (FIG. 1C) Changes in wake bout duration and frequency (in 24-hr period). (Pre: saline control before Hcrt-1, AW: active wake, QW: quite wake, nonREM: non-rapid eye movement sleep, REM: rapid eye movement sleep). All values are mean±SE; †p<0.05 compared to saline control, t-test; *p<0.05, **p<0.01, compared to pre-treatment level, Newman-Keuls test.

(FIG. 1A) A representative actigraph record (5 minute bins) showing the activity level during the 2 hr period following Hcrt-1 (3 µg/kg) and normal saline. Hcrt-1 produced an increase in motor activity within 5 minutes of injection that persisted for 60 minutes. (FIG. 1B) The increase of motor activity was statistically significant at 0-30 and 30-60 minutes after orexin administration, as compared to saline control. In (FIG. 1B) values are mean±SE, *p<0.05; **p<0.01, Newman-Keuls test.

DETAILED DESCRIPTION

I. Definitions

Figure 1A:
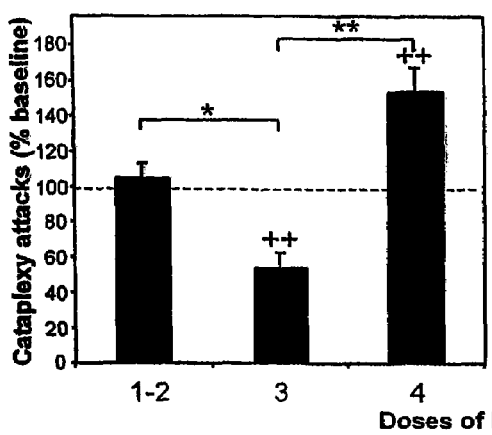
(FIG. 1A) Intravenous injection of Hcrt-1 produced a dose dependent change in cataplexy.

The term patient includes mammals, such as humans, domestic animals (e.g., dogs or cats), farm animals (cattle, horses, or pigs), monkeys, rabbits, rats, mice, and other laboratory animals.

The term molecule is used broadly to mean an organic or inorganic chemical such as a drug; a peptide, including a variant, analog, homolog, agonist, modified peptide or peptide-like substance such as a peptidomimetic or peptoid; or a protein such as an antibody or a fragment thereof, such as an $F_v$, $F_c$, or $F_{ab}$ fragment of an antibody, which contains a binding domain. A molecule can be nonnaturally occurring, produced as a result of in vitro methods, or can be naturally occurring, such as a protein or fragment thereof expressed from a cDNA library.

The terms polypeptide, peptide and protein are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

An agonist of a native polypeptide is a compound having a qualitative biological activity in common with the native polypeptide (described in detail below). For the purpose of the present invention, an "agonist" of a native Hcrt-1 or Hcrt-2 is defined by their ability to bind to the Hcrt-1 or Hcrt-2 receptor or related polypeptide respectively. For example, an agonist of Hcrt-1 or Hcrt-2 can bind to a native Hcrt-1 or Hcrt-2 receptor or related polypeptide, triggering intracellular events that either cause changes in membrane polarization, cause the release of other neurotransmitters or cause changes in the response to other neurotransmitters. The Hcrt-1 or Hcrt-2 agonists preferably have at least about 60%, more preferably at least about 70%, even more preferably at least about 80%, most preferably at least about 90% overall amino acid sequence identity with a native sequence Hcrt-1 or Hcrt-2 polypeptide, preferably a human Hcrt-1 or Hcrt-2 as described by Sakurai T., et al., 1998, Cell 92:573-85 and de Lecea, L., et al., 1998, Proc. Natl. Acad. Sci. U.S.A. 95:322-327 (Genbank REFSEQ Accession Nos. NM 001524, NM 001525 and NM 001526). The Hcrt-1 and Hcrt-2 agonists show at least about 80%, more preferably at least about 90% and most preferably at least about 95% or more amino acid sequence identity with the binding domain of the Hcrt-1 or Hcrt-2 polypeptide sequence, respectively. Fragments of native sequence Hcrt-1 or Hcrt-2 polypeptides from various mammalian species and sequences homologous to such fragments constitute another preferred group of Hcrt-1 and Hcrt-2 agonists. Such fragments preferably show at least about 80%, more preferably at least about 90%, most preferably at least about 95% or more sequence identity with the Hcrt-1 or Hcrt-2 polypeptide sequence. Another preferred group of Hcrt-1 or Hcrt-2 agonists is encoded by nucleic acid hybridizing under stringent conditions to the complement of nucleic acid encoding a native Hcrt-1 or Hcrt-2 polypeptide.

Stringent hybridization conditions are conditions under which a probe will hybridize to its target subsequence, typically in a complex mixture of nucleic acid, but not to other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

The Hcrt-1 and Hcrt-2 polypeptides of the present invention can be modified to provide a variety of desired attributes, e.g., with improved pharmacological characteristics, while increasing or at least retaining substantially all of the biological activity of the unmodified peptide. For example, the Hcrt-1 and Hcrt-2 peptides or fragments thereof can be modified by extending or decreasing the amino acid sequence of the peptide. Substitutions with different amino acids or amino acid mimetics can also be made.

The Hcrt-1 peptides employed in the subject invention need not be identical to peptides disclosed in the Example section, below, so long as the subject peptides are able to induce a same or similar response against the desired Hcrt receptor molecule or related molecule. Thus, a number of conservative substitutions (described in more detail below) can be made without substantially affecting the activity of Hcrt-1 or Hcrt-2.

Single amino acid substitutions, deletions, or insertions can be used to determine which residues are relatively insensitive to modification. Substitutions are preferably made with small, relatively neutral moieties such as Ala, Gly, Pro, or similar residues. The effect of single amino acid substitutions can also be probed using D-amino acids. The number and types of residues which are substituted or added depend on the spacing necessary between essential contact points and certain functional attributes which are sought (e.g., hydrophobicity versus hydrophilicity). Increased activity can also be achieved by such substitutions, compared to the native Hcrt peptide. In any event, such substitutions should employ amino acid residues or other molecular fragments chosen to avoid, for example, steric and charge interference which might disrupt binding.

The substituting amino acids, however, need not be limited to those naturally occurring in proteins, such as L-α-amino acids, or their D-isomers. The peptides can be substituted with a variety of moieties such as amino acid mimetics well known to those of skill in the art.

The individual residues of the Hcrt polypeptides can be incorporated in the peptide by a peptide bond or peptide bond mimetic. A peptide bond mimetic of the invention includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, *Chemistry and Biochemistry of Amino Acids, Peptides and Proteins*, Vol. VII (Weinstein ed., 1983). Several peptide backbone modifications are known, these include, ψ[CH$_2$S], ψ[CH$_2$NH], ψ[CSNH$_2$], ψ[NHCO], ψ[COCH$_2$] and ψ[(E) or (Z) CH=CH]. The nomenclature used above, follows that suggested by Spatola, above. In this context, ψ indicates the absence of an amide bond. The structure that replaces the amide group is specified within the brackets.

Amino acid mimetics can also be incorporated in the peptides. An amino acid mimetic as used here is a moiety other than a naturally occurring amino acid that conformationally and functionally serves as a substitute for an amino acid in a polypeptide of the present invention. Such a moiety serves as a substitute for an amino acid residue if it does not interfere with the ability of the peptide to illicit a response against the appropriate Hcrt receptor molecule. Amino acid mimetics can include non-protein amino acids, such as β-γ-δ-amino acids, β-γ-δ-imino acids (such as piperidine-4-carboxylic acid) as well as many derivatives of L-α-amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the present invention are discussed by Morgan and Gainor, (1989) *Ann. Repts. Med. Chem.* 24:243-252.

As noted above, the peptides employed in the subject invention need not be identical, but can be substantially identical, to the corresponding sequence of the target Hcrt receptor molecule or related molecule. The peptides can be subject to various changes, such as insertions, deletions, and substitutions, either conservative or non-conservative, where such changes might provide for certain advantages in their use. The polypeptides of the invention can be modified in a number of ways so long as they comprise a sequence substantially identical (as defined below) to a sequence in the naturally occurring Hcrt peptide molecule.

Alignment and comparison of relatively short amino acid sequences (less than about 30 residues) is typically straightforward. Comparison of longer sequences can require more sophisticated methods to achieve optimal alignment of two sequences. Optimal alignment of sequences for aligning a comparison window can be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci.* (*USA*) 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of sequence similarity over the comparison window) generated by the various methods is selected.

The term sequence identity means that two polynucleotide sequences are identical (i.e., on a nucleotide-by-nucleotide basis) over a window of comparison. The term "percentage of sequence identity" is calculated by comparing two optimally aligned sequences over the window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

As applied to polypeptides, the term substantial identity means that two peptide sequences, when optimally aligned, such as by the programs GAP or BESTFIT using default gap weights (described in detail below), share at least about 80 percent sequence identity, preferably at least about 90 percent sequence identity, more preferably at least about 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

A preferred example of an algorithm that is suitable for determining percent sequence identity and sequence similarity is the FASTA algorithm, which is described in Pearson, W. R. & Lipman, D. J., 1988, Proc. Natl. Acad. Sci. U.S.A. 85: 2444. See also W. R. Pearson, 1996, Methods Enzymol. 266: 227-258. Preferred parameters used in a FASTA alignment of DNA sequences to calculate percent identity are optimized, BL50 Matrix 15: −5, k-tuple=2; joining penalty=40, optimization=28; gap penalty −12, gap length penalty=−2; and width=16.

Another preferred example of algorithm that is suitable for determining percent sequence identity and sequence similarity are the BLAST and BLAST 2.0 algorithms, which are described in Altschul et al., 1977, Nuc. Acids Res. 25: 3389-3402 and Altschul et al., 1990, J. Mol. Biol. 215: 403-410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, 1989, Proc. Natl. Acad. Sci. U.S.A. 89: 10915) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, Proc. Natl. Acad. Sci. U.S.A. 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, 1987, J. Mol. Evol. 35: 351-360. The method used is similar to the method described by Higgins & Sharp, 1989, CABIOS 5: 151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., 1984, Nuc. Acids Res. 12: 387-395.

Another preferred example of an algorithm that is suitable for multiple DNA and amino acid sequence alignments is the CLUSTALW program (Thompson, J. D. et al., 1994, *Nucl. Acids. Res.* 22: 4673-4680). ClustalW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, 1992, *Proc. Natl. Acad. Sci. U.S.A.* 89: 10915-10919).

The term specific binding (and equivalent phrases) refers to the ability of a binding moiety (e.g., a receptor, antibody, Hcrt-1 or Hcrt-2 agonist, ligand or antiligand) to bind preferentially to a particular target molecule (e.g., ligand or antigen) in the presence of a heterogeneous population of proteins and other biologics (i.e., without significant binding to other components present in a test sample). Typically, specific binding between two entities, such as a ligand and a receptor, means a binding affinity of at least about $10^6$ $M^{-1}$, and preferably at least about $10^7$, $10^8$, $10^9$, or $10^{10}$ $M^{-1}$. Specific (or selective) binding can be assayed (and specific binding molecules identified) according to the method of U.S. Pat. No. 5,622,699; this reference and all references cited therein are incorporated herein by reference. Typically a specific or selective reaction according to this assay is at least about twice background signal or noise and more typically at least about 5 or at least about 100 times background, or more.

The term label or labeled refer to incorporation of a detectable marker, e.g., a radiolabeled amino acid or a recoverable label (e.g., biotinyl moieties that can be recovered by avidin or streptavidin). Recoverable labels can include covalently linked polynucleotide sequences that can be recovered by hybridization to a complementary sequence polynucleotide or PNA; such recoverable sequences typically flank one or both sides of a nucleotide sequence that imparts the desired activity, i.e., binding to an Hcrt receptor. Various methods of labeling PNAs and polynucleotides are known in the art and can be used. Examples of labels include, but are not limited to, the following: radioisotopes (e.g., $^3H$, $^{14}C$, $^{35}S$, $^{125}I$, $^{131}I$), fluorescent or phosphorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for antibodies, transcriptional activator polypeptide, metal binding domains, epitope tags). Labels can also be attached by spacer arms of various lengths, e.g., to reduce potential steric hindrance.

The term nighttime sleep consolidation refers to the nighttime sleep period that can be interrupted by up to ten brief awakenings in an individual. The individual is typically unaware of these arousals. In narcoleptics, many awakenings disrupt sleep. (There is no fixed rule for deciding how disrupted narcoleptic sleep needs to be for diagnostic purposes. Diagnosis is made on the basis of REM sleep onset, abnormally short sleep latency during the day and cataplexy; see, e.g., Chokroverty, S. (ed.), *Sleep Disorders Medicine: Basic Science, Technical Considerations, and Clinical Aspects*, 2$^{nd}$ edition, Butterworth Heinemann, Boston, Mass. U.S.A. 1999; Aldrich, M., *Sleep Medicine*, Oxford University Press, New York, N.Y. U.S.A. 1999). With normal aging, the number of nighttime sleep disruptions increase. Insomniacs have more than the typical amount of awakenings for their age as do Alzheimer's patients.

The term nighttime sleep architecture refers to nighttime sleep in an adult which can consist of a repeating, approximately 90 minute cycle of nonREM sleep-REM sleep periods. NonREM sleep includes periods of stages 1-4 nonREM sleep. With age, insomnia, narcolepsy and other sleep disorders, the amount of stage 4 sleep diminishes and can be completely absent.

II. General

The invention is premised, in part, on the result that administration of hypocretin-1 (Hcrt-1) produces an increase in activity level, longer waking periods, a decrease in REM sleep without change in nonREM sleep, reduced sleep fragmentation and/or a dose dependent reduction in cataplexy in canines with a hereditary form of narcolepsy. These and other results described in the Examples section lead to the conclusion that repeated administration of Hcrt-1 led to consolidation of waking and sleep periods and to a complete loss of cataplexy for periods of three or more days after treatment in animals that were never asymptomatic under control conditions. A particularly striking finding was that Hcrt-1 administration caused a consolidation of both sleep and waking states. The invention provides therapeutically effective dosage regimes for administering Hcrt-1 to patients having sleep disorders. Furthermore, the treatment regimes can employ similar dosages, routes of administration and frequency of administration to those used in treating canine narcoleptics. Although practice of the present methods is not dependent on an understanding of mechanism, the results provided by the application suggest that Hcrt-1 provides correlated improvements in cataplexy, waking duration and sleep continuity.

Because the daytime sleep deficit and related symptoms in narcolepsy so closely resemble the sleep deficit and other symptoms in other sleep disorders (e.g., REM sleep behavior disorder, restless legs syndrome, hypersomnia, insomnia, disrupted sleep in the elderly and other sleep disorders) characterized by daytime sleepiness, administration of a therapeutically effective dosage regime of Hcrt-1 is expected to reduce excessive daytime sleepiness and improve nighttime sleep consolidation and architecture in patients with these sleep disorders.

III. Sleep Disorders

A. General

There are a number of disorders that disturb sleep and cause patients to seek medical care (see, e.g., Chokroverty, S. (ed.), *Sleep Disorders Medicine: Basic Science, Technical Considerations, and Clinical Aspects*, $2^{nd}$ edition, Butterworth Heinemann, Boston, Mass. U.S.A. 1999; Aldrich, M., *Sleep Medicine*, Oxford University Press, New York, N.Y. U.S.A. 1999; these references and all references cited therein are herein incorporated by reference). These include narcolepsy, REM sleep behavior disorder, periodic movements during sleep, restless legs syndrome, circadian rhythm disorder, sleep apnea, hypersomnia and insomnia. Other medical disorders including Alzheimer's, depression and schizophrenia can also affect sleep. In these cases, the sleep abnormality can have a role in the etiology of the disease or can only be symptomatic. The sleep disorders described below can be treated by the methods described herein.

B. Narcolepsy

Narcolepsy is a chronic neurological disorder characterized by recurring episodes of sleep or sleepiness during the day, and often disrupted nocturnal REM sleep (see, e.g., Chokroverty, S. (ed.), *Sleep Disorders Medicine: Basic Science, Technical Considerations, and Clinical Aspects*, $2^{nd}$ edition, Butterworth Heinemann, Boston, Mass. U.S.A. 1999; Aldrich, M., *Sleep Medicine*, Oxford University Press, New York, N.Y. U.S.A. 1999). Symptoms of narcolepsy include abnormal sleep features, overwhelming episodes of sleep, excessive daytime somnolence (EDS), abnormal REM sleep, hypnagogic and hypnopompic hallucinations, disturbed nocturnal sleep, cataplexy, and sleep paralysis. EDS includes daytime sleep attacks, which may occur with or without warning; persistent drowsiness, which may continue for prolonged periods of time; and "microsleeps" or fleeting moments of sleep intruding into the waking state. Cataplexy is usually an abrupt and reversible decrease or loss of muscle tone most frequently elicited by emotion. It can involve a limited number of muscles or the entire voluntary musculature except the extraocular muscles and to some extent the diaphragm. Typically, the jaw sags, the head falls forward, the arms drop to the side, and/or the knees unlock, or the cataplectic human may fall completely on the ground. The duration of a cataplectic attack, partial or total, usually varies from a few seconds to thirty minutes. Attacks can be elicited by emotion, stress, fatigue, exercise or heavy meals. Sleep paralysis is an experience that occurs when an individual falls asleep or awakens, and is very akin to complete cataplectic episodes. Patients can find themselves suddenly unable to move, speak, open their eyes, or even breathe deeply. Hypnagogic hallucinations often involve vision, and the manifestations usually consist of simple forms (i.e., colored circles, parts of objects) that may be constant in size or changing, or may be quite complex in their scenario. Auditory hallucinations are also common and can range from a collection of sounds to an elaborate speech or melody. Hallucinations at sleep onset can involve elementary cenesthopathic (abnormal) sensations (e.g., prickling, rubbing, light touching), changes in location of body parts, or feelings of levitation or extracorporeal experiences. Patients having cataplexy without EDS are said to have isolated cataplexy. Other symptoms of narcolepsy besides EDS may or may not be present in such patients. Narcolepsy and isolated cataplexy are classified as separate indications by FDA. Nevertheless, this classification does not imply a separate basis. Both indications can be treated by the methods described in the application.

C. REM Sleep Behavior Disorder

REM sleep behavior disorder (RBD) is characterized by the intermittent loss of REM sleep electromyographic (EMG) atonia and by the appearance of elaborate motor activity associated with dream mentation.

Punching, kicking, leaping, and running from the bed during attempted dream enactment are frequent manifestations and usually correlate with the reported imagery.

Medical attention is often sought after injury has occurred to either the person or a bed partner. Occasionally, a patient may present because of sleep disruption. Because RBD occurs during REM sleep, it typically appears at least 90 minutes after sleep onset. Violent episodes typically occur about once per week but may appear as frequently as four times per night over several consecutive nights.

An acute, transient form can accompany REM rebound during withdrawal from alcohol and sedative-hypnotic agents. Drug-induced cases have been reported during treatment with tricyclic antidepressants and biperiden.

There can be a prodromal history of sleep talking, yelling, or limb jerking. Dream content can become more vivid, unpleasant, violent, or action-filled coincident with the onset of this disorder. Symptoms of excessive daytime sleepiness can appear if sufficient sleep fragmentation exists.

Some patients with this disorder also have narcolepsy, suggesting that there are common neurological causes of these disorders and that administration of a therapeutically effective dosage regime of Hcrt-1 can be effective for RBD as well.

D. Periodic Leg Movements in Sleep (PLMS) and Restless Legs Syndrome (RLS)

Periodic Leg Movements in Sleep (PLMS) is a sleep disorder that consists of periodic movements of the legs, feet, and/or toes during sleep. People with PLMS are often not aware of these movements, and often complain of several symptoms, including: insomnia; excessive daytime sleepiness (EDS); frequent awakenings from sleep, or unrefreshing sleep. Since EDS is associated with narcolepsy described above and administration of Hcrt-1 is effective in treating narcolepsy, PLMS can also be treated with a therapeutically effective dosage regime of Hcrt-1.

PLMS is frequently associated with a sleep disorder referred to as Restless Legs Syndrome (RLS). RLS is a disorder of the central nervous system that is characterized by unusual sensations in the legs and an overwhelming urge to move the legs while resting or attempting to fall asleep. Approximately 2% of the population in the U.S. suffer from RLS. Not all patients with PLMS also have RLS; however, most patients with RLS have PLMS. RLS is occasionally associated with pregnancy, anemia, or diabetes. Symptoms of RLS also can include: creeping or crawling sensations in the legs; an irresistible urge to move the affected extremity; relief of the symptoms by walking; a worsening of the symptoms when the afflicted person is at rest, particularly during the afternoon and evening hours. It has recently been reported that canine narcoleptics frequently have PLMS. Human narcoleptics can also have PLMS.

Since RLS is linked to narcolepsy and narcolepsy is caused by a deficiency in Hcrt release or in the response to Hcrt, RLS can be treated by administering a therapeutically effective dosage regime of Hcrt-1.

E. Circadian Rhythm Disorder

Circadian rhythm refers to a person's dark-light or sleep-wake pattern during a 24-hour cycle. Over 25 million Americans work the night shift or have nontraditional working schedules. Approximately 70% of these people suffer from Circadian Rhythm Disorder, an interruption in the biologic clock which results in a disruption in the regular intervals of sleeping and waking during a 24 hour-period. Circadian rhythm disorder can take different forms.

One form is Delayed Sleep Phase Syndrome (DSPS), in which the person goes to sleep later and, consequently, rises later than usual. This often interferes with normal work or school schedules. Symptoms can include: inadequate amounts of sleep; inability to fall asleep and difficulty awakening; impaired work performance, with chronic lateness or absences, difficulty concentrating, memory lapses.

Delayed sleep-phase syndrome (DSPS) is marked by: (1) sleep-onset and wake times that are intractably later than desired, (2) actual sleep-onset times at nearly the same daily clock hour, (3) little or no reported difficulty in maintaining sleep once sleep has begun, (4) extreme difficulty awakening at the desired time in the morning, and (5) a relatively severe to absolute inability to advance the sleep phase to earlier hours by enforcing conventional sleep and wake times. Typically, the patients complain primarily of chronic difficulty in falling asleep until between 2 a.m. and 6 a.m. or difficulty awakening at the desired or necessary time in the morning to fulfill social or occupational obligations. Daytime sleepiness, especially in the morning hours, occurs variably, depending largely on the degree of sleep loss that ensues due to the patient's attempts to meet his or her social obligations by getting up "on time." When not obliged to maintain a strict schedule (e.g. on weekends or during vacations), the patient sleeps normally but at a delayed phase relative to local time.

Patients with DSPS are usually perplexed that they cannot find a way to fall asleep more quickly. Their efforts to advance the timing of sleep onset (early bedtime, help from family or friends in getting up in the morning, relaxation techniques, or the ingestion of hypnotic medications) yield little or no effect at all in aiding sleep onset and may only aggravate the daytime symptoms of difficulty awakening and sleepiness. Chronic dependence on hypnotics or alcohol for sleep is unusual but, when present, complicates the clinical situation. More commonly, patients give a history of having tried multiple sedating agents, which were abandoned because of only transient efficacy.

Another form of circadian rhythm disorder is Advanced Sleep Phase Syndrome (ASPS), in which the person experiences excessive sleepiness in the early evening and has a very early awakening time. Patients with ASPS often complain about difficulty staying awake in evening social situations and insomnia at the end of the sleep period, with early morning awakening.

Advanced sleep-phase syndrome is marked by a person's intractable and chronic inability to delay the onset of evening sleep or extend sleep later into the morning hours by enforcing more conventional social sleep and wake times. The major presenting complaint can concern either the inability to stay awake in the evening, or early morning awakening insomnia, or both. Unlike other sleep maintenance disorders, the early morning awakening occurs after a normal amount of otherwise undisturbed sleep. In pure cases, there is no major mood disturbance during the waking hours. Unlike in other cases of excessive sleepiness, daytime school or work activities are not affected by somnolence. However, evening activities are routinely curtailed by the need to retire much earlier than the social norm. Typical sleep-onset times are between 6 p.m. and 8 p.m., and no later than 5 a.m. These sleep-onset and wake times occur despite the patient's best efforts to delay sleep to later hours.

Negative personal or social consequences can occur due to leaving activities in the early to mid-evening hours in order to go to sleep. Attempts to delay sleep onset to a time later than usual can result in falling asleep during social gatherings, or can have more serious consequences, such as drowsiness or falling asleep while driving in the evening. Afflicted individuals who attempt to work evening or night shifts would presumably have marked difficulty staying awake during the evening and early morning hours. If patients are chronically forced to stay up later for social or vocational reasons, the early-wakening aspect of the syndrome could lead to chronic sleep deprivation and daytime sleepiness or napping.

The potent and long lasting arousing effects of Hcrt-1 are likely to be effective in entraining patients to the desired circadian phase. The phase achieved would be dependent upon the time of drug administration.

F. Sleep Apnea

Sleep Apnea is a sleep disorder in which a person repeatedly stops breathing for short periods during sleep, often without being aware of the cessations of breath. An obstructed airway is the most common cause of the apnea. Approximately 12 million Americans have sleep apnea, which is more common in men than in women. Symptoms can include: brief interruption of breathing periodically during sleep; extremely loud snoring that is interrupted by pauses and gasps; choking sensations during sleep; falling asleep at inappropriate times during the day, such as while driving, working, or talking; awakening with headaches in the morning.

In sleep apnea, relaxation of the muscles of the tongue and the soft palate at the base of the throat, allows the breathing passage to collapse in individuals with a narrow airway. Although chest movements may continue, no air flows into the lungs and oxygen levels in the blood decrease. When blood oxygen levels fall too low, the person briefly wakes to take a breath. This gasping breath can produce a loud, characteristic snort. The cycle of sleeping, airway collapsing, waking, and sleeping repeats, often hundreds of times in a night. Individuals with sleep apnea do not remember these brief awakenings and believe they slept through the night. However, the interrupted sleep leaves the individual exhausted in the morning and sleepy throughout the day. If left untreated, sleep apnea may also cause cardiovascular problems and greatly shorten life span.

Central sleep apnea syndrome is characterized by a cessation or decrease of ventilatory effort during sleep and is usually associated with oxygen desaturation.

This disorder is usually associated with a complaint of insomnia with an inability to maintain sleep; however, excessive sleepiness can also occur. Several awakenings during the course of the night usually occur, sometimes with a gasp for air for evaluation because of observations by a concerned bed partner. Feelings of daytime tiredness, fatigue, and sleepiness are common. Central sleep apnea syndrome can have a few associated obstructive apneas and episodes of hypoventilation; however, the predominant respiratory disturbance consists of central apneic episodes.

Snoring can occur but is not prominent. The hemodynamic complications of this syndrome can include the development of cardiac arrhythmias, pulmonary hypertension, and cardiac failure. These hemodynamic findings can reflect a primary disorder of the cardiovascular system that leads to the development of the apnea. Difficulties with memory and other cognitive functions can result from the excessive sleepiness. Headaches upon awakening are common in patients with severe alteration of blood gases during sleep. Depressive reactions can also occur.

The invention provides methods for treating the excessive daytime tiredness, fatigue, and sleepiness associated with sleep apnea by administering a therapeutically effective dosage regime of Hcrt-1.

G. Hypersomnia

Idiopathic hypersomnia is a sleep disorder that is associated with a normal or prolonged major sleep episode and excessive sleepiness consisting of prolonged (1 to 2 hour) sleep episodes of nREM sleep.

Idiopathic hypersomnia can be characterized by a complaint of constant or recurrent excessive daytime sleepiness, typically with sleep episodes lasting 1 or more hours in duration. It can be enhanced in situations that allow sleepiness to become manifest, such as reading or watching television in the evening. The major sleep episode can be prolonged, lasting more than 8 hours. The capacity to arouse the subject can be normal, but some patients report great difficulty waking up and experience disorientation after awakening.

Some patients complain of paroxysmal episodes of sleepiness culminating in sleep attacks, as in narcoleptic patients described above. Most often these attacks are preceded by long periods of drowsiness. Naps are usually longer than in narcolepsy or sleep apnea, and short naps are generally reported as being nonrefreshing. Often as disabling as narcolepsy, idiopathic hypersomnia has an unpredictable response to stimulants such as the amphetamines and methylphenidate hydrochloride. These patients often report more side effects, such as tachycardia or irritability, and the use of stimulants tend to exacerbate the associated symptoms of headache.

Associated symptoms suggesting dysfunction of the autonomic nervous system are not uncommon. They include headaches, which may be migrainous in quality; fainting episodes (syncope); orthostatic hypotension; and, most commonly, peripheral vascular complaints.

The invention provides methods for treating the long periods of drowsiness that accompanies hyposomnia by administering a therapeutically effective dosage regime of Hcrt-1.

H. Insomnia

Insomnia is the difficulty in initiating or maintaining sleep. This term is employed ubiquitously to indicate any and all gradations and types of sleep loss. Insomnia is generally characterized by disrupted nighttime sleep, with frequent arousals, reduced or absent stage 4 sleep and in some cases frequent daytime napping.

Chronically poor sleep in general leads to decreased feelings of well-being during the day. There is a deterioration of mood and motivation, decreased attention and vigilance, low levels of energy and concentration, and increased fatigue.

Mild insomnia is described as an almost nightly complaint of an insufficient amount of sleep or not feeling rested after the habitual sleep episode. It is accompanied by little or no evidence of impairment of social or occupational functioning. Mild insomnia often is associated with feelings of restlessness, irritability, mild anxiety, daytime fatigue, and tiredness.

Moderate insomnia can be described as a nightly complaint of an insufficient amount of sleep or not feeling rested after the habitual sleep episode. It can be accompanied by mild or moderate impairment of social or occupational functioning. Moderate insomnia always is usually associated with feelings of restlessness, irritability, anxiety, daytime fatigue, daytime sleepiness and tiredness.

Severe insomnia can be described as a nightly complaint of an insufficient amount of sleep or not feeling rested after the habitual sleep episode. It can be accompanied by severe impairment of social or occupational functioning. Severe insomnia is usually associated with feelings of restlessness, irritability, anxiety, daytime fatigue, and tiredness.

The invention provides methods for treating the daytime fatigue and daytime sleepiness that accompanies insomnia by administering a therapeutically effective dosage regime of Hcrt-1.

I. Other Disorders

1. Alzheimer's Depression

Alzheimer's is a degenerative disease causing diffuse neurodegeneration and resultant loss of memory, reasoning ability and ability to care for oneself. In its later stages, disorientation, fragmented sleep and insomnia manifest as "sundowning" or nighttime wandering behavior are characteristic and are frequent cause of institutionalization. Daytime sleepiness is also a correlate of Alzheimer's. The daytime sleepiness, nighttime sleep disruption and neurodegeneration all overlap with what is known about the pathophysiology and anatomy of narcolepsy.

A degeneration of the hypocretin system or a deficiency of hypocretin release may be linked to the occurrence of these symptoms as it is in narcolepsy. The invention provides methods for treating Alzheimer's by administering a therapeutically effective dosage regime of Hcrt-1.

2. Depression

Depression is characterized by a pervasive feeling of sadness or helplessness, suicidal impulses and a loss of interest in previously pleasurable activities. It is also frequently characterized by daytime sleepiness, short sleep latency and disrupted nighttime sleep. A shortened latency to REM sleep is characteristic as the case in narcolepsy. These sleep disturbances are strikingly similar to those seen in narcolepsy. Narcoleptics are significantly more likely than age and sex matched controls to be depressed with some studies calculating that nearly 50% of narcoleptics are depressed.

This overlap of specific sleep abnormalities and psychological manifestations between narcolepsy and depression indicates that common mechanisms must link these disorders. Therefore, the invention provides methods for treating depression by counteracting the short REM sleep latency and daytime sleepiness and by consolidating nighttime sleep by administering a therapeutically effective dosage regime of Hcrt-1.

3. Schizophrenia

Schizophrenia is a group of severe emotional disorders characterized by misinterpretation and retreat from reality, delusions, hallucinations, inappropriate emotional affect, and withdrawn, bizarre or regressive behavior.

Several aspects of schizophrenia overlap with narcolepsy (Siegel et al., 1999, J. Neuroscience 19: 48-257). Narcolepsy and schizophrenia may co-exist in patients. The characteristic hallucinations of schizophrenia can resemble the hypnagogic hallucinations of narcolepsy. Age of onset is similar in narcolepsy and schizophrenia, typically in the second or third decade for both diseases. Both diseases are characterized by degenerative changes in the limbic system, a region heavily innervated by hypocretin neurons. REM sleep at sleep onset is also characteristic of both disorders. Finally disrupted nighttime sleep and daytime sleepiness can be characteristic of schizophrenia, as in narcolepsy.

These similarities of sleep and behavior suggest similar underlying pathology in these two disorders. Therefore the invention provides methods for treating schizophrenia by administering a therapeutically effective regime of Hcrt-1.

IV. Patients Amenable to Treatment

Patients amenable to treatment include patients who are presently asymptomatic but who are at risk of developing a sleep disorder, e.g., symptomatic narcolepsy or isolated cataplexy, at a later time. Such individuals include those having relatives who have experienced a sleep disorder, and those whose risk is determined by analysis of genetic or biochemical markers, or by biochemical methods. Other patients amenable to treatment can include patients wherein the administration of the treatment ameliorates, prevents, or reduces one or more symptoms of one or more sleep disorders within hours or months of treatment. Patients to receive treatment can also include individuals who are not diagnosed with any sleep disorder.

Genetic markers of risk for developing a particular sleep disorder have been determined. For example, genetic markers of risk for developing narcolepsy include the presence of the HLA allele, HLADQB1*0602. The HLA-DQB1*0602 allele has also been linked to subclinical abnormal nocturnal REM sleep and increased daytime sleepiness in normal subjects as well as certain schizophrenia subtypes (see, e.g., Mignot, E., et al., *Sleep* (1999) 22(3): 347-352; Cadieux, R., et al., *J. Clin. Psychol.* (1985) 46: 191-193; Douglass, A., et al., *J. Nerv. Ment. Dis.* (1991) 179: 12-17; these references and all references cited therein are herein incorporated by reference). The presence or absence of HLA-DQB1*0602 can be determined by standard procedures (see, e.g., Mignot, E., et al., *Sleep* (1999) 22(3): 347-352, U.S. Pat. Nos. 5,908,749, 5,565,548, 5,541,065, 5,196,308; these references are herein incorporated by reference. Other markers include a mutation or deletion in any Hypocretin (Orexin) Receptor gene, the prepro-Hypocretin (Orexin) gene itself, or in the Hypocretin (Orexin) Receptor 1 or Hypocretin (Orexin) Receptor 2 gene. Additional risk factors for narcolepsy and/or cataplexy include having Niemann-Pick disease type C or Norrie's disease.

Biochemical markers of risk can include a defect in the proteolytic processing of the prepro-orexin precursor of the known hypocretin (orexin) molecules, or in the posttranslational modification mechanism that results in the abnormal production of Hcrt-1 (orexin-A) and Hcrt-2 (orexin-B) molecules. Other biochemical markers of risk for narcolepsy include autoantibodies or activated lymphocytes in the blood in individuals free of other immune-mediated and/or neoplastic diseases, or the presence of specific autoantibodies in individuals with or without other immune-mediated and/or neoplastic diseases. The presence of such markers in asymptomatic individuals signifies that the processes leading to narcolepsy or cataplexy is almost certainly underway, although has not yet progressed so far as to produce symptoms.

In asymptomatic individuals, treatment of sleep disorders can begin at any age including antenatally, or at birth. For example, in narcolepsy, treatment is usually begun before an individual is 45 years old because if an individual has not developed narcolepsy or isolated cataplexy by that time, he or she probably will not do so at all. If a biochemical marker of disease, such as an autoantibody or activated T cell is detected, treatment should usually begin shortly thereafter. If the likelihood of developing a sleep disorder, such as narcolepsy and or cataplexy is based on relatives having the disease or detection of a genetic marker, treatment can also be administered shortly after identification of these risk factors, or shortly after diagnosis. Alternatively, an individual found to possess a genetic marker can be left untreated but subjected to regular monitoring for biochemical or symptomatic changes without treatment. The decision whether to treat immediately or to monitor symptoms depends in part on the extent of risk predicted by the genetic marker(s) found in the individual for a particular sleep disorder. Once begun, a therapeutically effective dosage regime of Hcrt-1 is typically continued at intervals for a period of a week, a month, three months, six months or a year. In some patients, treatment is administered for up to the rest of a patient's life. Treatment can generally be stopped if a biochemical risk marker disappears. In veterinary patients, such as dogs having a hereditary form of narcolepsy, treatment is usually begun at anytime between birth to five months of age.

Other individuals amenable to treatment show or have shown behavioral symptoms of a sleep disorder (i.e., symptomatic patients) (see, e.g., Chokroverty, S. (ed.), *Sleep Disorders Medicine: Basic Science, Technical Considerations, and Clinical Aspects*, $2^{nd}$ edition, Butterworth Heinemann, Boston, Mass. U.S.A. 1999; Aldrich, M., *Sleep Medicine*, Oxford University Press, New York, N.Y. U.S.A. 1999). Such symptoms can be detected by any of the techniques described below. In addition, symptomatic patients often have biochemical or genetic risk factors as described for asymptomatic individuals. In symptomatic patients, treatment usually begins at or shortly after diagnosis of symptoms. Treatment is typically continued at intervals for a week, a month, six months, a year or up to the rest of the patient's life. Typically, the patient's symptoms are monitored. If monitoring indicates a sustained reduction or elimination of symptoms for a period of at least a month, and preferably at least three months, treatment can be terminated or reduced in dosage. Monitoring is continued and treatment is resumed if symptoms reappear or worsen. If treatment causes no significant amelioration of symptoms in a patient for a period of at least six months, and typically at least one year, or if the side effects of the treatment are intolerable to a patient, then treatment can be discontinued.

V. Diagnostic and Monitoring Methods

A. Monitoring Methods

Overt symptoms of sleep disorders can be detected as described by, e.g., Chokroverty, S. (ed.), *Sleep Disorders Medicine: Basic Science, Technical Considerations, and Clinical Aspects*, $2^{nd}$ edition, Butterworth Heinemann, Boston, Mass. U.S.A. 1999; Aldrich, M., *Sleep Medicine*, Oxford University Press, New York, N.Y. U.S.A. 1999; these references and all references cited therein are herein incorporated by reference. The monitoring can include conducting a nocturnal polysomnogram (PSG), Multiple Sleep Latency Test (MSLT), Epworth Sleepiness Scale (EPS) questionnaire, Maintenance of Wakefulness Test (MWT), pupilography, electroencephalograms, electroencephalographic spectral analysis, actigraphy, or maintaining a log of incidence of cataplexy or any other sleep disorder symptom including their number, severity and duration.

B. Diagnostic Methods

Figure 4:
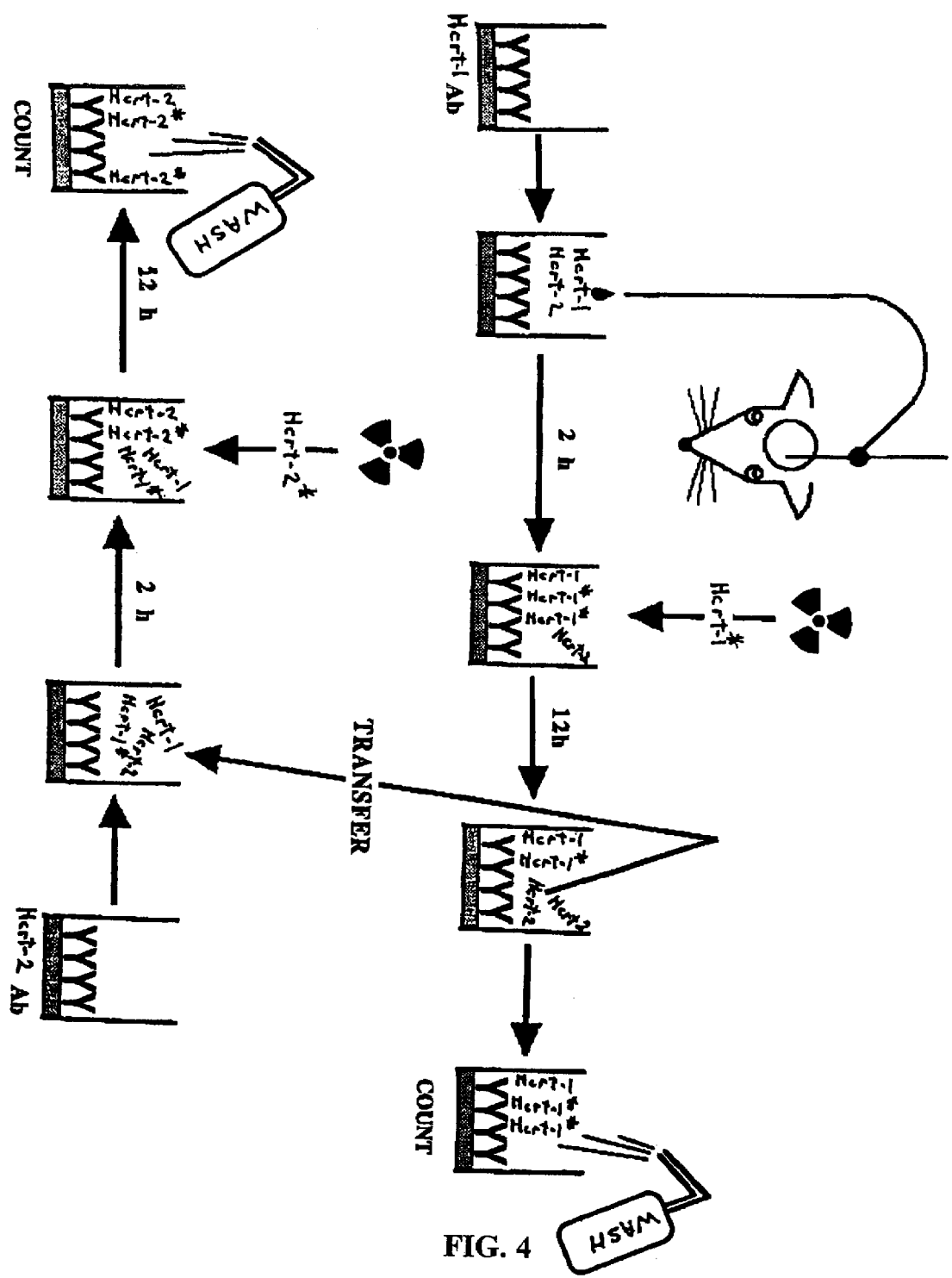
FIG. 4. The protocol for a sequential multiple antigen radioimmunoassay for hypocretin-1 (Hcrt-1) and hypocretin-2 (Hcrt-2). Sample or standard is loaded into wells onto which antiserum for Hcrt-1 has been pre-adsorbed via protein-A. Subsequently, radiolabeled Hcrt-1 (Hcrt-1*) is added to the wells. Competition for the antiserum then ensues between Hcrt-1 and Hcrt-1* The contents of the wells are then transferred to new wells onto which antiserum for Hcrt-2 has been preadsorbed and the procedure repeated but with radiolabeled Hcrt-2 (Hcrt-2*). The previous wells are washed and counted for bound radioactivity.

A modified solid-phase radioimmunoassay (RIA) can be used for diagnostic purposes. As described in Example 3 and shown in FIG. 4, a solid-phase RIA can be used for measurement of Hcrt-1 or Hcrt-2 in cerebrospinal fluid (CSF) and plasma. The presence, absence, or change in Hcrt-1 and/or Hcrt-2 levels in CSF or plasma can indicate degenerative changes in the Hcrt system.

The above diagnostic test works by comparing a measured level of Hcrt-1 or Hcrt-2 in a patient with a baseline level determined in a control population of patients unaffected by a particular sleep disorder. A significant departure between the measured level in a patient and baseline levels in unaffected persons signals a positive outcome of the diagnostic test. A departure is considered significant if the measured value falls outside the range typically observed in unaffected individuals due to inherent variation between individuals and experimental error. For example, a departure can be considered significant if a measured level does not fall within the mean plus one standard deviation of levels in a control population. In some methods, a departure between a measured level and control levels is judged significant if the measured level is at least the level of the 75th, 80th or 95th percentile of a control population. In other words, the measured level in the patient occurs in only 50%, 25%, 20% or 5% of normal individuals. If the measured level of Hcrt-1 or Hcrt-2 does not differ significantly from baselines levels in a control population, the outcome of the diagnostic test is considered negative.

Depending on the particular procedure used, Hcrt-1 can be directly labeled as with isotopes, chromophores, lumiphores, chromogens, or indirectly labeled such as with biotin to which a streptavidin complex can later bind. Hcrt-1 can also be unlabeled.

VI. Treatment Regimes

Hcrt-1 administration produces dramatic and correlated improvements in cataplexy, waking duration and sleep continuity. The suppression of REM sleep seen after systemic Hcrt administration exactly mirrors the selective suppression of REM sleep seen after intracerebroventricular administration of Hcrt-1 (Hagan et al., 1999) and is further evidence for the central action of intravenously administered Hcrt-1. The invention also provides methods of administering a therapeutically effective dosage regime of Hcrt-1 to a peripheral tissue of a patient for treatment of other sleep disorders characterized by daytime sleepiness and interrupted nighttime sleep, such as sleep fragmentation in the elderly and in other disorders of arousal.

In therapeutic applications, compositions or medicants are administered to a patient suffering from a sleep disorder, such as narcolepsy or cataplexy, until there is a reduction in excessive daytime sleepiness and an improvement in nighttime sleep consolidation and architecture. In therapeutically effective regimes, Hcrt-1 is usually administered in several dosages until a sufficient response has been achieved. Typically, the treatment is monitored and repeated dosages can be given. Hcrt-1 is not usually labeled.

The amount of Hcrt-1 that can be combined with a carrier material to produce a single dosage form vary depending upon the disease treated, the type of drug, the mammalian species, and the particular mode of administration. As a general guide, suitable unit doses for Hcrt-1 of the present invention, for example, can contain between 2.1 µg/kg/week to about 17.5 µg/kg/week of the active compound. An exemplary unit dose is between 0.3 µg/kg to about 2.5 µg/kg. An alternative unit dose, corresponds to between 0.05 µg/kg to about 10 µg/kg, depending on the individual. Such unit doses can be administered more than once a day, for example 1, 2, 3, 4, 5 or 6 times a day, so that the total daily dosage for a 70 kg adult is in the range of about 21 µg to about 4200 µg. Such unit doses can also be administered every 24 hours. Some such unit doses can also be administered at least every 12 hours. A typical dosage can be a 210 µg tablet taken once a day, or, multiple times per day (for example, a 105 µg tablet taken twice per day), or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release. Such therapy can extend for a number of weeks or months, and in some cases, years.

The specific dose level for any particular patient can depend on a variety of factors including the activity of the specific compound employed; the age, body weight, general health, sex and diet of the individual being treated; the time and route of administration; the rate of metabolism or excretion; other drugs which are concurrently or have previously been administered; and the severity of the particular disease undergoing therapy.

In some instances, dosages outside the above ranges are used to interrupt, adjust, or terminate treatment in conjunction with individual patient response.

For therapeutically effective dosage regimes of Hcrt-1 used in the methods of the present invention, a therapeutically effective dose for humans can be estimated initially from non-human animal models.

Toxicity and therapeutic efficacy of the compounds described herein can be determined by standard pharmaceutical procedures in experimental animals, e.g., by determining the $LD_{50}$, (the dose lethal to 50% of the population tested) and the $ED_{50}$ (the dose therapeutically effective in 50% of the population tested). The dose ratio between toxic and therapeutic effect is the therapeutic index and can be expressed as the ratio between $LD_{50}$ and $ED_{50}$. Compounds which exhibit high therapeutic indices are preferred. The data obtained from these nonhuman animal studies can be used in formulating a dosage range that is not toxic for use in humans. The dosage of such compounds lies preferably within a range of circulating concentrations that include the $ED_{50}$ with little or no toxicity. The exact formulation, route of administration and dosage can be chosen by the individual physician in view of the patient's condition. (See, e.g., Fingl et al. (1975) In: *The Pharmacological Basis of Therapeutics*, Ch. 1).

VII. Pharmaceutical Compositions and Methods of Administration

Hcrt-1 can be delivered or administered to a mammal, e.g. a human patient or subject, alone, in the form of a pharmaceutically acceptable salt or hydrolyzable precursor thereof, or in the form of a pharmaceutical composition wherein the compound is mixed with suitable carriers or excipient(s) in a therapeutically effective amount. A therapeutically effective regime means that a drug or combination of drugs is administered in sufficient amount and frequency and by an appropriate route to at least detectably prevent, delay, inhibit or reverse development of at least one symptom or biochemical marker of a sleep disorder. A "therapeutically effective amount", "pharmacologically acceptable dose", "pharmacologically acceptable amount" means that a sufficient amount of Hcrt-1 or combination of Hcrt-1 with other agents is present to achieve a desired result, e.g., preventing, delaying, inhibiting or reversing a symptom or biochemical markers of a sleep disorder when administered in an appropriate regime. In a preferred embodiment, a sufficient amount of Hcrt-1 is present to prevent, delay, inhibit or reverse a symptom or biochemical markers of a sleep disorder or the progression of a sleep disorder when administered in an appropriate regime.

Hcrt-1 and other active agents that are used in the methods of the present invention can be administered as pharmaceutical compositions comprising Hcrt-1, together with a variety of other pharmaceutically acceptable components. Pharmaceutical compositions can be in the form of solids (such as powders, granules, dragees, tablets or pills), semi-solids (such as gels, slurries, or ointments), liquids, or gases (such as aerosols or inhalants).

Suitable formulations for use in the present invention are found in *Remington's Pharmaceutical Sciences* (Mack Publishing Company (1985) Philadelphia, Pa., 17$^{th}$ edition) and Langer, *Science* (1990) 249:1527-1533, which are incorporated herein by reference. The pharmaceutical compositions described herein can be manufactured in a conventional manner, i.e., mixing, dissolving, granulating, dragee-making, levigating, emulsifying, encapsulating, entrapping or lyophilizing processes.

In preparing the formulations of the present invention, pharmaceutically recognized equivalents of each of the compounds can be alternatively used. These pharmaceutically recognized equivalents can be pharmaceutically acceptable salts or pharmaceutically acceptable acid addition salts.

A pharmaceutically acceptable salt is a non-toxic alkali metal, alkaline earth metal, or an ammonium salt commonly used in the pharmaceutical industry including a sodium, potassium, lithium, calcium, magnesium, barium, ammonium, and protamine zinc salt, which is prepared by methods well known in the art. The term also includes a non-toxic acid addition salt, which is generally prepared by reacting the compounds of the present invention with a suitable organic or inorganic acid. Representative salts include hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and napsylate.

A pharmaceutically acceptable acid addition salt is a salt which retains the biological effectiveness and properties of the free bases and which is not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like (see, e.g., Bundgaard, H., ed., *Design of Prodrugs* (Elsevier Science Publishers, Amsterdam 1985)).

Hcrt-1 and other active agents can be formulated with common excipients, diluents or carriers, and compressed into tablets, or formulated as elixirs or solutions for convenient oral administration. Hcrt-1 and other active agents can also be formulated as sustained release dosage forms and the like.

In order to exert the desired therapeutic or prophylactic effects, Hcrt-1 and other active agents of the invention must reach brain cells and brain tissue requiring their passage from the blood to the brain by crossing the microcapillary membranes of the cerebrovascular endothelium (also referred to as the blood-brain barrier or BBB). The invention provides methods for administering a therapeutically effective dosage regime of Hcrt-1 and other active compounds of the invention to a peripheral tissue in a patient (i.e., tissues other than central nervous system tissues). This can be achieved in various ways, including oral, buccal, rectal, parenteral, intraperitoneal, intradermal, transdermal, intratracheal, and intramuscular administration. Moreover, Hcrt-1 and other active agents can be administered in a local rather than systemic manner, in a depot or sustained release formulation. In addition, Hcrt-1 and Hcrt-2 can be administered in a liposome.

For injection, Hcrt-1 along with other active agents of the invention can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, for injection, the compounds of the present invention can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the Hcrt-1 along with other active agents can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in a conventional manner.

For administration by inhalation, the compounds for use according to the present invention are conveniently delivered in the form of an aerosol spray preparation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Hcrt-1 and other active agents of the invention can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oil-based or aqueous vehicles, and can contain formulator agents such as suspending, stabilizing and/or dispersing agents. The compositions are formulated as sterile, substantially isotonic and in full compliance with all Good Manufacturing Practice (GMP) regulations of the U.S. Food and Drug Administration.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Hcrt-1 and other active agents can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds can be employed. Liposomes and emulsions are well known examples of delivery vehicles or carriers for hydrophobic drugs. In some methods, long-circulating, i.e., stealth, liposomes can be employed. Such liposomes are generally described in Woodle, et al., U.S. Pat. No. 5,013,556, the teaching of which is hereby incorporated by reference. The compounds of the present invention can also be administered by controlled release means and/or delivery devices such as those described in U.S. Pat. Nos. 3,845,770; 3,916,899; 3,536,809; 3,598,123; and 4,008,719; the disclosures of which are hereby incorporated by reference.

Certain organic solvents such as dimethylsulfoxide (DMSO) also can be employed, although usually at the cost of greater toxicity. Additionally, the compounds can be delivered using a sustained-release system, such as semipermeable matrices of solid hydrophobic polymers containing the therapeutic agent. Various types of sustained-release materials have been established. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The therapeutically effective amounts for the methods of the present invention can depend on the subject being treated, on the subject's weight, the subject's overall health, the severity of the affliction, the manner of administration and the judgment of the prescribing physician.

VIII. Kits

The invention further provides kits comprising hypocretin 1 (Hcrt-1), hypocretin 2 or both hypocretin 1 and 2. Usually, the kit also contains instructions for carrying out the methods of the invention.

IX. References

Aldrich M S (1992) Narcolepsy. Neurology 42(suppl 6): 34-43.

Aldrich M S (1998) Diagnostic aspects of narcolepsy. Neurology 50:S2-S7.

Bliwise D (1994) Dementia. In: Principles and practice of sleep medicine (Kryger, M H, Roth T, Dement W C eds) Vol. 2, pp 790-800 (Philadelphia: W.B. Saunders).

Chemelli R M, Willie J T, Sinton C M, Elmquist J K, Scammell T, Lee C, Richardson J A, Williams S C, Xiong Y, Kisanuki Y, Fitch T E, Nakazato M, Hammer R E, Saper C B, Yanagisawa M (1999) Narcolepsy in orexin knockout mice: molecular genetics of sleep regulation. Cell 98:437-451.

Chen C-T, Harrison T A, Dun S L, Hwang L L, Dun N J, Chang J-K (1999) Intracisternal administration of orexins increased blood pressure and heart rate in urethane anesthetized rats. Soc Neurosci Abst 25:12

Dube M G, Kalra S P, Kalra P S (1999) Food intake elicited by central administration of orexin/hypocretins: identification of hypothalamic sites of action. Brain Res. 842: 473-477.

Hagan J J, Leslie R A, Patel S, Evans M L, Wattam T A, Holmes S, Benham C D, Taylor S G, Routledge C, Hemmati P, Munton R P, Ashmeade T E, Shah A S, Hatcher J P, Hatcher P D, Jones D N C, Smith M I, Piper D C, Hunter A J, Porter R A, Upton N (1999) Orexin A activates locus coeruleus cell firing and increases arousal in the rat. Proc Natl Acad Sci U.S.A. 96:10911-10916.

Horvath T L, Peyron C, Dialno S, Ivanov A, Aston-Jones G, Kilduff T S, van den Pol A N (1999) Hypocretin (Orexin) activation and synaptic innervation of the locus coeruleus noradrenergic system. J Comp Neurol 415:145-159.

Ida T, Nakahara K, Katayama T, Murakami N, Nakazato M (1999) Effect of lateral cerebroventricular injection of the appetite-stimulating neuropeptide, orexin and neuropeptide Y, on the various behavioral activities of rats. Brain Res 821:526-529.

Kastin A J, Akerstrom V (1999) Orexin A but not orexin B rapidly enters brain from blood by simple diffusion. J Pharmacol Exp Ther 289:219-223.

Kirchgessner A L, Liu M (1999) Orexin synthesis and response in the gut. Neuron 24:941-951.

Kiyashchenko L I, Mileykovskiy B Y, Siegel J M. (2000) Hypocretin microinjections in the vicinity of locus coeruleus change muscle tone in decerebrate rats. Sleep (In press).

Lai Y Y, Siegel J M (1988) Medullary regions mediating atonia. J Neurosci 8:4790-4796.

Lin L, Faraco J, Li R, Kadotani H, Rogers W, Lin X-Y, Qiu X-H, de Jong P J, Nishino S, Mignot E (1999) The REM sleep disorder canine narcolepsy is caused by a mutation in the hypocretin (orexin) receptor gene. Cell 98:365-376.

Lucas E A, Foutz A S, Dement W C, Mitler M M (1979) Sleep cycle organization in narcoleptic and normal dogs. Physiol Behav 23:737-743.

Maidment, N. T., Brumbaugh, D. R., Rudolph, V. D., Eredlyi, E. and Evans, C. J. (1989) Microdialysis of extracellular endogenous opioid peptides from rat brain in vivo. Neuroscience 33: 549-557.

Maidment, N. T., Siddal, B. J., Rudolph, V. D, Eredlyi, E. and Evans, C. J. (1991) Dual determination of extracellular cholecystokinin and neurotensin fragments in rat forebrain: microdialysis combined with a sequential multiple antigen radioimmunoassay. Neuroscience 45: 81-93.

Maidment, N. T. and Evans, C. J. Measurement of extracellular neuropeptides in the brain: Microdialysis linked to solid-phase radioimmunoassays with subfemtomole limits of detection. In: Microdialysis in the Neurosciences, pp. 275-303. T. E. Robinson & J. B. Justice, Jr., Eds., (1991), Elsevier Science Publishers.

Mitler M M, Dement W C (1977) Sleep studies on canine narcolepsy: pattern and cycle comparisons between affected and normal dogs. Electroenceph and Clin Neurophysiol 43:691-699.

Nishino S, Ripley B, Overeem S, Lammers G J, Mignot E (2000) Hypocretin (orexin) deficiency in human narcolepsy. The Lancet 355:39-40.

Siegel J M, Nienhuis R, Fahringer H M, Paul R, Shiromani P, Dement W C, Mignot E, Chiu C (1991) Neuronal activity in narcolepsy: identification of cataplexy-related cells in the medial medulla. Science 252:1315-1318.

Takahashi N, Okumura T, Yamada H, Kohgo Y (1999) Stimulation of gastric acid secretion by centrally administered orexin-A in conscious rats. Biochem Biophys Res Commun 254:623-627.

Wu M-F, Gulyani S A, Yau E, Mignot E, Phan B, Siegel J M (1999). Locus coeruleus neurons: cessation of activity during cataplexy. Neuroscience 91:1389-1399.

Yamanaka A, Sakurai T, Katsumoto T, Yanagisawa M, Goto K (1999) Chronic intracerebroventricular administration of orexin-a to rats increases food intake in daytime, but has no effect on body weight. Brain Research 849:248-252.

EXAMPLES

Materials and Methods

Six genetically narcoleptic Doberman pinschers (5 males and 1 female) served as subjects. We analyzed the effect of systemically administered Hcrt-1 on cataplexy with a modified food elicited cataplexy test (FECT). The effect of Hcrt-1 administration on sleep organization was determined using polygraph recording. The effect of Hcrt-1 administration on activity levels and the duration of sleep-waking states over the 24-hr period was determined with actigraphy.

One to 4 µg/kg of Hcrt-1 (orexin-A, #003-30, Phoenix Pharmaceuticals, Mountain View, Calif.) dissolved in normal saline (100 µg in 2 ml) was administered through the cephalic vein using a glass syringe. The glass syringe was pre-soaked in 1% BSA, rinsed in Milli-Q water, then dried at 60° C. prior to use. This treatment combined with the large volume of the dilutent used minimizes problems caused by the "stickiness" of the peptide. On control days, saline was administered in the same manner. Hcrt-1 or control injections were administered daily at the same time.

Cataplexy Test

FECT was done by introducing a bowl of soft food (Pedigree, by Kalkan) in the home cage and counting the number of cataplectic attacks (including hind limb collapse and total cataplexies in which all four limbs collapse and the whole body contacts the floor) and total time required to eat the food (FECT time). All the FECTs began 4 min after the administration of Hcrt-1 or saline.

Sleep-Wake Study

Polygraphic recording. Electrodes for the assessment of sleep-wake parameters (EEG, EMG, EOG and hippocampal theta) were chronically implanted in two dogs as described earlier (Siegel et al., 1991). Polygraphic variables were recorded for 4 hrs after Hcrt-1 (3 µg/kg) or saline injection.

Actigraphy

The effects of Hcrt-1 on sleep-wake periods were monitored continuously for 24 hrs/day with collar mounted actigraphs (Actiwatch, Mini Mitter Inc, Sundriver, Oreg.) while the animals remained in their home dog runs. Actigraphs were secured to a neck collar that was placed on the dogs throughout the period of study. Data were downloaded to a PC through an inductively coupled Actiwatch reader and further analyzed by a program of our design. The program could integrate total numbers of movements above a preset amplitude for a measurement of total level of activity in 5 minutes epochs. For analysis of sleep state, actigraphs were first calibrated by placing them on an animal instrumented for conventional polygraphic recording. A threshold was determined for discriminating polygraphically defined waking and sleep in 30-sec epochs. The durations of sleep periods were then counted and tabulated by computer. The sleep-wake bouts measured by actigraph correlated well with hypnograms obtained from polygraphic recording ($r=0.84$, $p<0.001$).

Data Analysis

Data were analyzed with ANOVA, followed by post-hoc comparisons using Newman-Keuls tests. Bonferroni t-tests were done to compare the effect of Hcrt-1 on sleep stages measured with polygraphic recording. One sample t-tests were performed to test the significance of number of cataplectic attacks and FECT time (expressed as a percentage of baseline) after Hcrt-1 within each dose.

Example 1

Changes in Cataplexy After Hcrt-1 Treatment

Figure 1B:
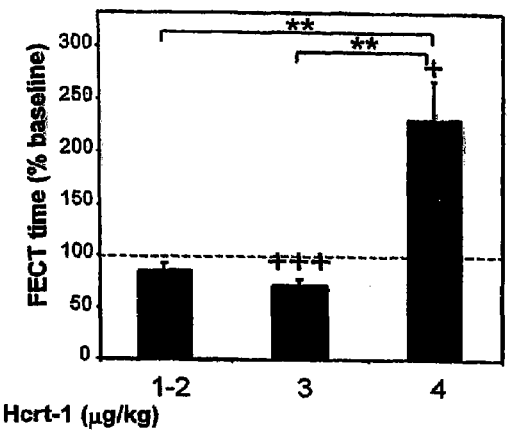
(FIG. 1B) FECT time also showed a dose dependent change. Doses of 1 and 2 µg/kg did not affect cataplexy. Doses of 3 µg/kg produced a significant decrease in the number of falls (FIG. 1A) and in the time it took to consume the food (eating time+cataplexy time) (FIG. 1B). In contrast, 4 µg/kg doses significantly increased the number of falls (FIG. 1A) and the time required to consume the food (FIG. 1B) relative to baseline (dotted line).

Hcrt-1 administration had a significant effect on cataplexy in a dose dependent manner (number of cataplectic attacks, $p<0.005$, $F=7.98$, $df=2, 14$; FECT time, $p<0.001$, $F=17.15$, $df=2, 14$; ANOVA). The 1 and 2 µg/kg doses of Hcrt-1 did not produce any change in cataplexy (FIG. 1a). The 3 µg/kg dose produced a significant ($p<0.001$, $df=7$; t-test) reduction in cataplexy and a significant ($p<0.001$, $df=7$; t-test) reduction in the FECT time (FIG. 1b). The 4 µg/kg dose of Hcrt-1 significantly increased the severity of cataplexy compared to saline control ($p<0.01$, $df=7$; t-test) and significantly increased the FECT time ($p<0.05$, $df=7$; t-test).

Figure 1C:
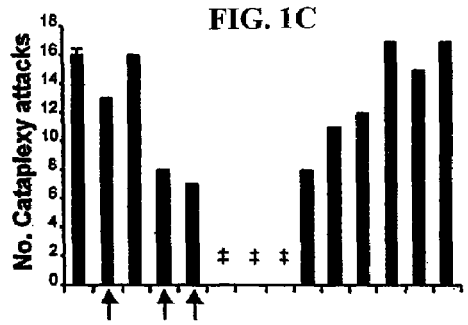
(FIG. 1C-D) In the two dogs tested with repeated doses of Hcrt-1, a complete suppression of cataplexy resulted following the last dose.
Figure 1D:
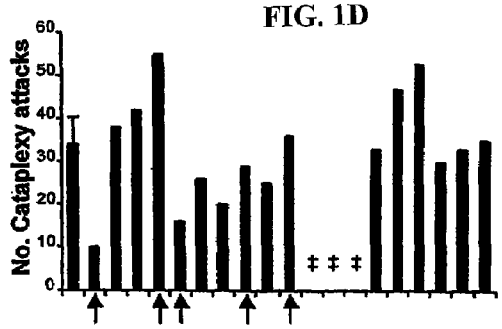
Figure 1C:
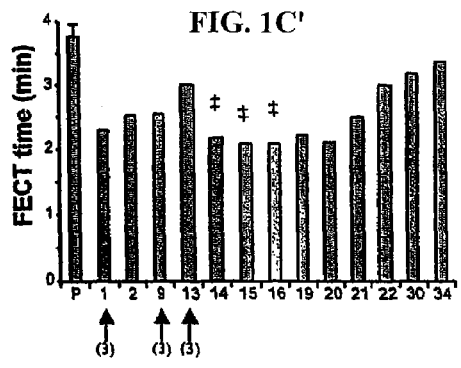
Figure 1D:
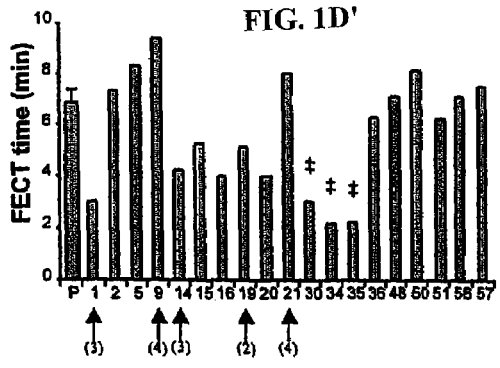

Two of the 3 dogs treated with repeated doses of Hcrt-1 went for 3 or more days without any cataplexy after the administration of 3-5 doses of Hcrt-1 (FIGS. 1c and 1d). A total absence of cataplexy had never been observed for even one day in any of the 3 dogs in 35 consecutive previous baseline tests in each animal. During the period without cataplexy the animals showed normal feeding during FECTs. The time taken to finish the food was significantly reduced due to the absence of cataplexy attacks ($p<0.02$ $df=5$; Bonferroni t-test). In both dogs, the severity of cataplexy gradually returned to pretreatment levels over a 3-4 day period (FIGS. 1c' and 1d').

Example 2

Effect of Hcrt-1 on Sleep-Wake Periods and Activity Level

Polygraphic recording of sleep-wake parameters showed that the same dose of Hcrt-1 that induced a reduction in cataplexy produced a significant reduction ($p<0.05$, $df=2$; Bonferroni t-test) in REM sleep during the 4 hr post-injection period as compared to saline controls (FIG. 2a).

Actigraph measurements were used to calculate the duration of sleep and waking states for the nights following injection. First, comparisons of actigraphic measurements and polygraphically recorded sleep states were made and used to determine thresholds for distinguishing sleep and wake periods. Then wake and sleep state periods were quantified starting 2 hrs following administration. We found that after a single dose of Hcrt-1 the mean duration of both sleep periods and wake periods increased. These effects lasted for more than 24 hrs ($p<0.01$, $F=5.56$, $df=3$, 15 and $p<0.002$, $F=8.58$, $df=3$, 15 for sleep and wake periods respectively). The frequency of sleep and wake bouts was reduced ($p<0.05$, $F=3.35$, $df=3$, 15 and $p<0.05$, $F=3.40$, $df=3$, 15, respectively) (FIG. 2b, 2c). The total duration of sleep was increased after Hcrt-1 as compared to pre-drug levels, but not significantly ($p=0.055$, $df=5$; t-test). During the periods of cataplexy suppression following repeated Hcrt-1 doses, sleep was also consolidated (increased sleep bout length) relative to baseline conditions ($p<0.05$, $df=5$; t-test).

Figure 3A:
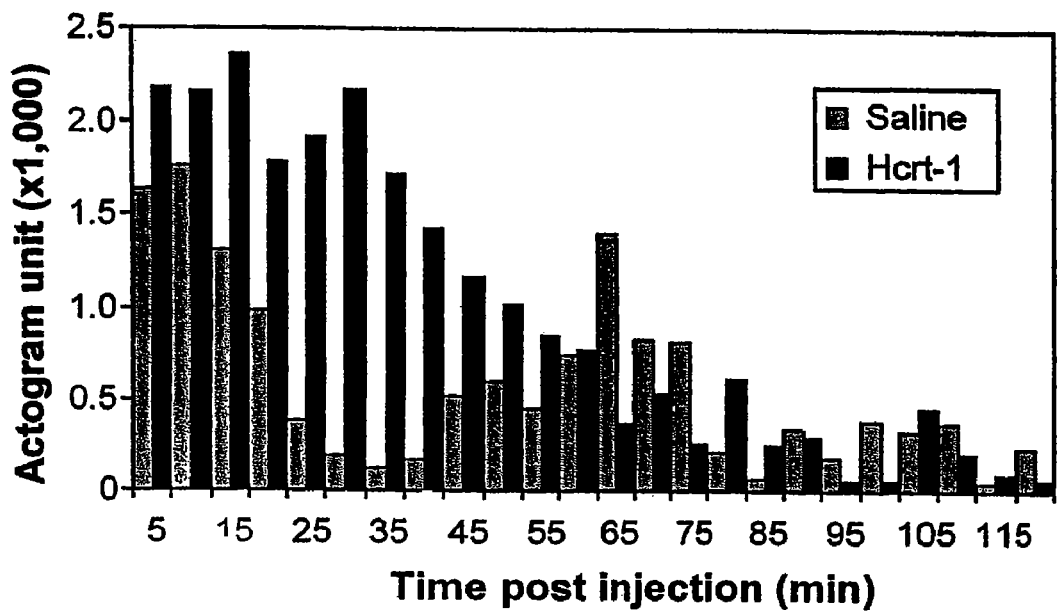
FIG. 3. Acute changes in motor activity after Hcrt-1 administration.
Figure 3B:
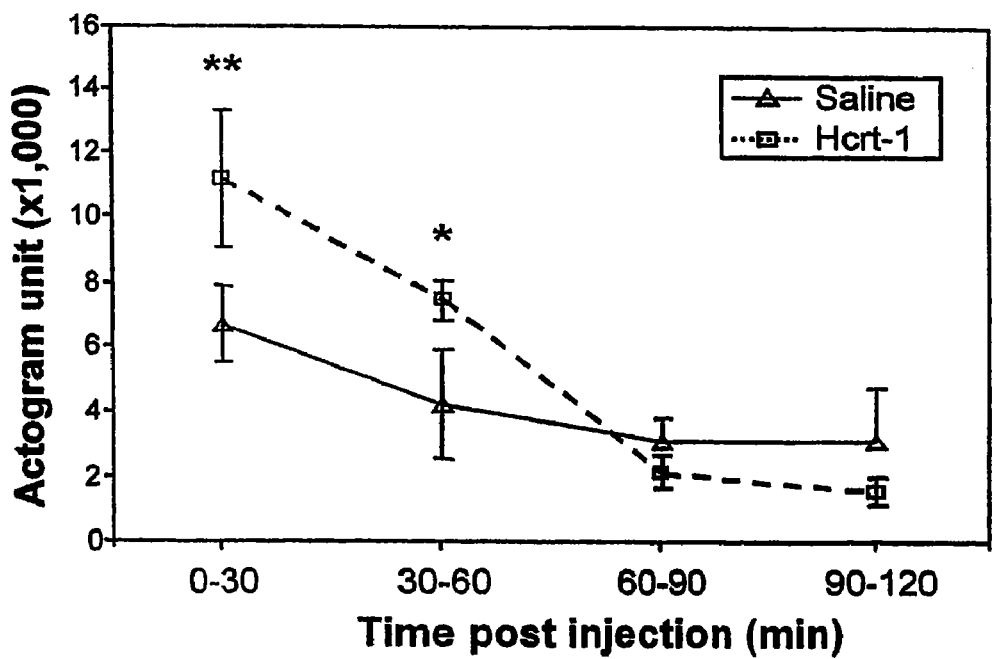

Hcrt-1 injection produced increased motor activity in the first 30 minutes after injection. The differences in amplitude of motor activity following Hcrt-1 and saline injection diminished over the following 60 minutes (FIGS. 3a, 3b).

Example 3

Solid-Phase Radioimmunoassay (RIA) for Hypocretin (Hcrt-1)

In order to assess the effect of the intravenous Hcrt-1 injection on central levels of the compound, cerebrospinal fluid (CSF) and blood serum was collected and analyzed after infusion of Hcrt-1. In these studies, Hcrt-1 was injected intravenously as in the behavioral studies into two Doberman pinschers, one narcoleptic, and one control that had been anesthetized with Fluothane anesthesia. Saline was injected in a third dog, a non-narcoleptic control. Prior to injection and at 15, 30 min and one hour intervals after injection, CSF was collected from the cisterna magna with a spinal needle and then quickly frozen at −20. Hypocretin was extracted from 0.5-1 ml samples with reverse a phase SEP-PAK C18 column. An $^{125}$I Hcrt-1 radioimmunoassay was used to measure levels in reconstituted aliquots (described below).

In commonly used RIA procedures the competition between radiolabeled and unlabeled sample-derived peptide for the antibody takes place with all three components in solution. Separation of antibody-bound from free tracer peptide is subsequently accomplished either by precipitation of the antibodies (for example by using polyethylene glycol or a second antibody), or alternatively by adsorption of the free tracer peptide with charcoal. In addition to the time consuming nature of these separation steps (they all require incubation, centrifugation and decanting of supernatant) there is a problem of non-specific entrapment of tracer in the pellet.

In the solid-phase immunoassays previously developed for measurement of opioid peptides, neurotensin and cholecystokinin in brain microdialysates (Maidment et al., 1989; Maidment et al, 1991; Maidment and Evans, 1991), no precipitation step is required and non-specific binding is greatly reduced. Furthermore, sensitivity is increased over that obtained with more traditional methods using identical antibodies and assay volumes. In this system, the antibody is immobilized onto the surface of 96-well Immulon II-coated plates (Dynatech) through attachment of the constant region of the immunoglobulin (Ig) molecule to the purified bacterial wall protein-protein A (the use of this protein greatly increases the capacity of the wells for antibody thereby avoiding the necessity for antibody purification). Competition for the exposed antigenic sites of the antibody between labeled and unlabeled peptide is then initiated (greatest sensitivity is achieved by pre-incubation of sample or standard peptide). After a pre-determined incubation period separation of bound from free tracer peptide is accomplished by simply pouring out the contents of the wells and washing with buffer. For example, the individual wells of a 96-well plate containing Ab-bound tracer peptide are then physically separated and counted in a gamma counter. This published procedure has been modified herein to enable measurement of Hcrt-1 in CSF and plasma.

The Hcrt-1, iodinated Hcrt-1, and Hcrt-1 antiserum were obtained from Phoenix Pharmaceuticals, Inc. (530 Harbor Blvd, Belmont, Calif.). Dynex Microlite 2 Plus 96-well plates (Fisher) to which is added microscint-20 (Packard) after the final wash. This enables direct reading of radioactivity in a Top Count plate reader (Packard) without the requirement to separate out individual wells.

The IC$_{50}$ value for this Hcrt-1 assay is 2 fmole with a limit of detection of 0.1 fmole.

Apart from the advantages of convenience and sensitivity afforded by this method, another significant advance originates from the negligible non-specific binding associated with the use of the plates. This characteristic enables the transfer of individual well contents prior to the final wash (i.e., sample plus iodinated peptide) into wells containing immobilized antibody to a second peptide. In this way it is possible to sequentially assay several different peptides in a single biological sample. For instance it can be possible to measure the two forms of Hcrt-1 in a single sample of CSF or plasma. (This has been termed sequential multiple antigen radioimmunoassay technique, or "SMART").

Prior to RIA, Hcrt-1 is extracted from the CSF or plasma sample. This is achieved by acidification of the sample with 1% TFA followed by loading onto a C18 Sep-Column, washing the column with 1% TFA, and eluting the peptide with 1% TFA/40% acetonitrile. The eluant is then dried down and re-suspended in RIA buffer ready for assay.

Preparation of the Plates and Assay Protocol

The 96-well plates are first coated with protein A(Sigma, binding capacity 9-11 mg of human IgG per mg) by adding 0.1 µg in 100 µl of 0.1M sodium bicarbonate, pH9, to each well. The plates are normally prepared in advance and can be stored for several weeks at 4° C. when tightly wrapped to prevent drying out. However, it is possible to use them after approximately 2 h incubation at room temperature. The protein A solution is then discarded and the plates washed 3 times in a wash buffer consisting of 0.15M K2HPO4, 0.2 mM ascorbic acid, 0.2% Tween 20, pH7.5 and blotted on a paper towel. Next, 200 µl of assay buffer (same as wash buffer plus 0.1% gelatin) is pipetted into each well and left at room temperature for 30 min. This step is included in an attempt to remove protein A bound with only low affinity to the plate which might otherwise dissociate at later stages in the assay thereby removing bound antibody and tracer. After dumping this solution and blotting, 50 µl of the appropriate concentration of antibody diluted with assay buffer is added to all but 4 wells. To these 4 wells are added assay buffer alone to provide an index of non-specific binding. The antibody dilution used is that which is pre-determined to produce 20-30% maximum binding in the assay. The wells are then left for 2 h at room temperature.

Standard solutions of Hcrt-1 are prepared in quadruplet ranging from 0.1 to 50 fmol in 50 µl. These standards (plus four blanks) are made up in RIA buffer. All dilutions are carried out in polypropylene tubes to minimize loss due to 'sticking'. The contents of each tube are then transferred to the assay wells following dumping of the antibody solution, washing 3 times with wash buffer and blotting.

A 2 h pre-incubation period at room temperature then follows. At the end of this time 50 µl of assay buffer containing approximately 5,000 CPM of $^{125}$I-labeled tracer peptide is added to each well and the plate left to incubate overnight at 4° C. (this final incubation step can be reduced to approx. 2 h with only slight loss of sensitivity). Subsequently the contents of the wells are discarded and the wells washed 3 times with wash buffer and blotted prior to addition of Microscint 20 and counting in the Top Count plate reader. Results from the Solid-Phase Radioimmunoassay (RIA) for Hypocretin (Hcrt-1) are shown below in Table I:

TABLE I

| Animal | Substance | Number of samples | Mean level fmol/ml | Range in levels fmol/ml |
|---|---|---|---|---|
| Narcoleptic dog | Cerebrospinal fluid | 22 | 53 | 26-140 |
| Narcoleptic dog | Blood serum | 12 | 11 | 5-16 |
| Normal human | Cerebrospinal fluid | 35 | 62 | 21-203 |
| Normal human | Blood serum | 3 | 10 | 8-14 |

Discussion

A therapeutically effective dosage regime of Hcrt-1 can reduce or totally eliminate cataplexy for extended periods of time. High doses of Hcrt-1 produced a significant increase in cataplexy. A dramatic long-term suppression of cataplexy was seen after repeated administrations of Hcrt-1 in two of the dogs that had never shown such a hiatus in cataplexy occurrence. During the period of suppression the dogs consumed their food at a normal rate for a non-cataplectic dog, demonstrating that the Hcrt-1 did not act by appetite suppression or by inducing illness. The dogs appeared in excellent health throughout the study. There were no grooming, "wet dog shakes" or other abnormal behaviors that have been reported after central administration of high doses of Hcrt (Ida et al., 1999; Yamanaka et al., 1999).

One of the cardinal signs of narcolepsy is daytime sleepiness, resulting in frequent intrusions of sleep into the waking period, followed by disrupted nighttime sleep, with waking intrusion resulting in short mean sleep intervals (Mitler and Dement, 1977; Aldrich, 1992). This has been reported not only in human narcoleptics, but also in canine narcoleptics (Mitler and Dement, 1977; Lucas et al., 1979). Hcrt-1 administration normalized both waking and sleep, resulting in longer waking periods, a higher level of activity and more continuous sleep periods. This linkage between reduction in cataplexy and consolidation of sleep-wake periods was seen not only on the days of Hcrt-1 administration, but also on the days of cataplexy cessation following repeated Hcrt-1 administrations.

Narcoleptic dogs are known to have a mutation in the gene that synthesizes the Hcrt-2 receptor (Lin et al., 1999). This mutation can either result in the receptor being non-functional or having altered function. The effectiveness of Hcrt-1 administration suggests that the receptor can be synthesized and remain responsive to its agonist at a reduced level. The therapeutic effectiveness of Hcrt-1 administration can also be due to stimulation of the Hcrt-1 receptor or to activation of other as yet unidentified Hcrt receptors. The longer-term reduction in symptoms, which followed repeated administrations of Hcrt-1, is thought to be linked to downregulation of aminergic and cholinergic receptors, which are upregulated in both canine and human narcolepsy (Aldrich, 1992), presumably secondary to the reduced function of the Hcrt system.

The present invention is not to be limited in scope by the exemplified embodiments which are intended as illustrations of single aspects of the invention. Indeed, various modifications of the invention in addition to those described herein will become apparent to those skilled in the art from the foregoing description and accompanying drawings. Such modifications are intended to fall within the scope of the appended claims.

All publications and patent documents cited above are hereby incorporated by reference in their entirety for all purposes to the same extent as if each were so individually denoted.

What is claimed is:

1. A method of treating a patient having narcolepsy or cataplexy comprising:
peripherally administering a therapeutically effective dosage regime of hypocretin-1 to the patient in need thereof, whereby the hypocretin-1 crosses the blood brain barrier of the patient and thereby treats the narcolepsy or cataplexy in the patient.

2. The method of claim 1, wherein the hypocretin-1 is a natural human hypocretin-1.

3. The method of claim 1, wherein the patient experiences a reduction in excessive daytime sleepiness responsive to administering the therapeutically effective dosage regime.

4. The method of claim 1, wherein the patient experiences an improvement in nighttime sleep consolidation and architecture responsive to the treatment.

5. The method of claim 1, further comprising monitoring the condition of the patient responsive to administering the therapeutically effective dosage regime.

6. The method of claim 1, wherein the patient is a mammal.

7. The method of claim 1, wherein the hypocretin-1 is peripherally administered to the patient by intravenous delivery, intraperitoneal delivery, transdermal delivery, intramuscular delivery, subcutaneous delivery, inhalation, or oral delivery.

8. A method of treating narcolepsy/cataplexy comprising:
peripherally administering to a patient having narcolepsy or cataplexy a therapeutically effective dosage regime of hypocretin-1, and
monitoring the condition of the patient responsive to the treatment, wherein the monitoring indicates a reduction in excessive daytime sleepiness (EDS) and an improvement in nighttime sleep consolidation and architecture.

9. The method of claim 8, wherein the patient is a mammal.

10. The method of claim 9, wherein the mammal is human.

11. The method of claim 8, wherein the hypocretin-1 is free of a label.

12. The method of claim 8, wherein the dosage in the regime is separated by at least 12 hours.

13. The method of claim 8, wherein the dosage in the regime is separated by at least 24 hours.

14. The method of claim 8, wherein each dosage is 0.3 to about 10 μg/kg of hypocretin-1.

15. The method of claim 8, wherein the dosage regime is peripherally administered to the patient by intravenous delivery, intraperitoneal delivery, transdermal delivery, intramuscular delivery, subcutaneous delivery, inhalation, or oral delivery.

16. The method of claim 8, wherein the monitoring is selected from the group consisting of conducting nocturnal polysomnogram (PSG), Multiple Sleep Latency Test (MLST), Epworth Sleepiness Scale (EPS) questionnaire, Maintenance of Wakefulness Test (MWT), pupilography, electroencephalograms, electrocephalographic spectral analysis, actigraphy, and maintaining a log of incidence of cataplexy including their number, severity and duration.

17. The method of claim 8, wherein the method further comprises identifying a patient in need of treatment for one or more sleep disorders prior to administration of said therapeutically effective dosage regime.

18. The method of claim 8, wherein hypocretin-1 is administered together with a pharmaceutically acceptable carrier as a pharmaceutical composition.

* * * * *